United States Patent
Hart et al.

(10) Patent No.: US 7,207,971 B2
(45) Date of Patent: Apr. 24, 2007

(54) PRESSURE RELIEF DEVICES FOR USE WITH BALLOON CATHETERS

(75) Inventors: Colin P. Hart, Queensbury, NY (US); James L. Fehl, Salem, NY (US); Glenn H. Wadleigh, Queensbury, NY (US); Ronald West, Fort Ann, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 641 days.

(21) Appl. No.: 10/328,372

(22) Filed: Dec. 23, 2002

(65) Prior Publication Data

US 2004/0122361 A1 Jun. 24, 2004

(51) Int. Cl.
*A61M 29/00* (2006.01)

(52) U.S. Cl. .................................. 604/97.01

(58) Field of Classification Search ... 604/96.01–100.3
See application file for complete search history.

(56) References Cited

U.S. PATENT DOCUMENTS

| | | |
|---|---|---|
| 3,402,717 A | 9/1968 | Doherty |
| 3,548,805 A | 12/1970 | Datsenko et al. |
| 4,044,793 A | 8/1977 | Krueger et al. |
| 4,276,874 A | 7/1981 | Wolvek et al. |
| 4,370,982 A | 2/1983 | Reilly |
| 4,439,185 A | 3/1984 | Lundquist |
| 4,583,978 A | 4/1986 | Porat et al. |
| 4,743,230 A | 5/1988 | Nordquest |
| 4,758,223 A | 7/1988 | Rydell |
| 4,808,165 A | 2/1989 | Carr |
| 4,832,692 A * | 5/1989 | Box et al. ............... 604/99.01 |
| 4,919,121 A | 4/1990 | Rydell et al. |
| 4,929,238 A | 5/1990 | Baum |
| 4,944,726 A | 7/1990 | Hilal et al. |
| 5,007,919 A | 4/1991 | Silva et al. |
| 5,015,233 A | 5/1991 | McGough et al. |
| 5,057,078 A | 10/1991 | Foote et al. |
| 5,059,176 A | 10/1991 | Winters |
| 4,813,934 A | 5/1992 | Engelson et al. |
| 5,137,514 A | 8/1992 | Ryan |
| 5,147,300 A | 9/1992 | Robinson et al. |
| 5,213,115 A | 5/1993 | Zytkovicz et al. |
| 5,226,880 A | 7/1993 | Martin |
| 5,284,480 A | 2/1994 | Porter et al. |
| 5,290,260 A | 3/1994 | Stines |
| 5,306,248 A | 4/1994 | Barrington |
| 5,312,340 A | 5/1994 | Keith |

(Continued)

FOREIGN PATENT DOCUMENTS

DE  297 12 332 U1  11/1997

(Continued)

*Primary Examiner*—LoAn H. Thanh
(74) *Attorney, Agent, or Firm*—Crompton, Seager & Tufte, LLC

(57) ABSTRACT

A pressure relief mechanism is incorporated into a modified syringe-type inflation device that may be coupled to a balloon catheter for inflating and deflating the balloon. An engagement mechanism selectively engages and disengages from a threaded shaft for advancing or withdrawing a plunger placed in slidable, yet sealing fit within a cylindrical chamber. In a first engaging position, the threaded shaft may be forcibly advanced or withdrawn in the cylindrical chamber, while in a second disengaged position, the plunger may be quickly pulled back.

15 Claims, 17 Drawing Sheets

U.S. PATENT DOCUMENTS

| | | |
|---|---|---|
| 5,342,304 A | 8/1994 | Tacklind et al. |
| 5,429,606 A | 7/1995 | Robinson et al. |
| 5,441,484 A | 8/1995 | Atkinson et al. |
| 5,443,447 A | 8/1995 | Kassis |
| 5,445,615 A | 8/1995 | Yoon |
| 5,454,788 A | 10/1995 | Walker et al. |
| 5,466,221 A | 11/1995 | Zadini et al. |
| 5,507,727 A | 4/1996 | Crainich |
| 5,545,133 A | 8/1996 | Burns et al. |
| 5,685,848 A | 11/1997 | Robinson et al. |
| 5,713,242 A * | 2/1998 | Kanner et al. ............ 74/424.78 |
| 5,741,229 A | 4/1998 | Robinson et al. |
| 5,752,935 A | 5/1998 | Robinson et al. |
| 5,785,685 A | 7/1998 | Kugler et al. |
| 5,800,405 A | 9/1998 | McPhee |
| 5,860,955 A | 1/1999 | Wright et al. |
| 5,919,162 A | 7/1999 | Burns |
| 5,938,642 A | 8/1999 | Burroughs et al. |
| 6,050,973 A | 4/2000 | Duffy |
| 6,063,057 A * | 5/2000 | Choh ..................... 604/99.01 |
| 6,102,890 A | 8/2000 | Stivland et al. |
| 6,110,143 A | 8/2000 | Kamen |
| 6,110,151 A | 8/2000 | Spool et al. |
| 6,179,815 B1 | 1/2001 | Foote |
| 6,234,996 B1 | 5/2001 | Bagaoisan et al. |
| 6,325,777 B1 | 12/2001 | Zadno-Azizi et al. |
| 6,325,778 B1 | 12/2001 | Zadno-Azizi et al. |
| 6,458,096 B1 | 10/2002 | Briscoe et al. |
| 6,468,243 B1 | 10/2002 | Miyagawa et al. |
| 2002/0133116 A1 | 9/2002 | Davis et al. |

FOREIGN PATENT DOCUMENTS

| | | |
|---|---|---|
| EP | 0 217 559 B1 | 4/1987 |
| EP | 0 565 045 A1 | 10/1993 |
| EP | 0 962 21 A1 | 8/1999 |
| WO | WO 98/56440 A1 | 12/1998 |

* cited by examiner

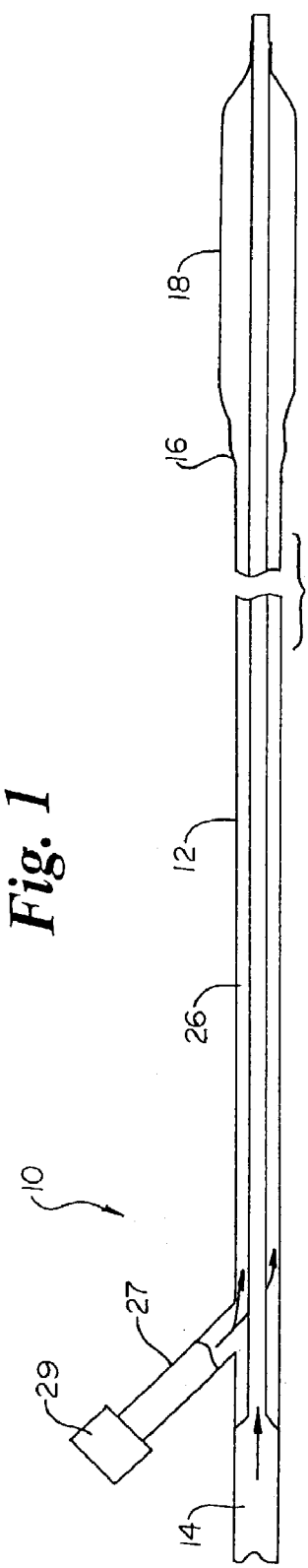
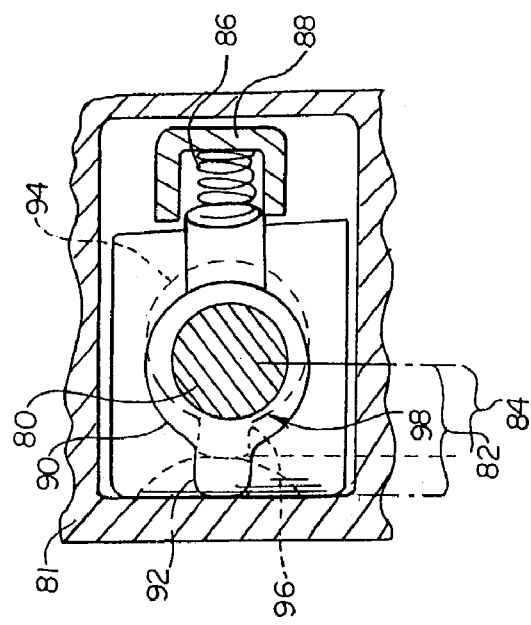

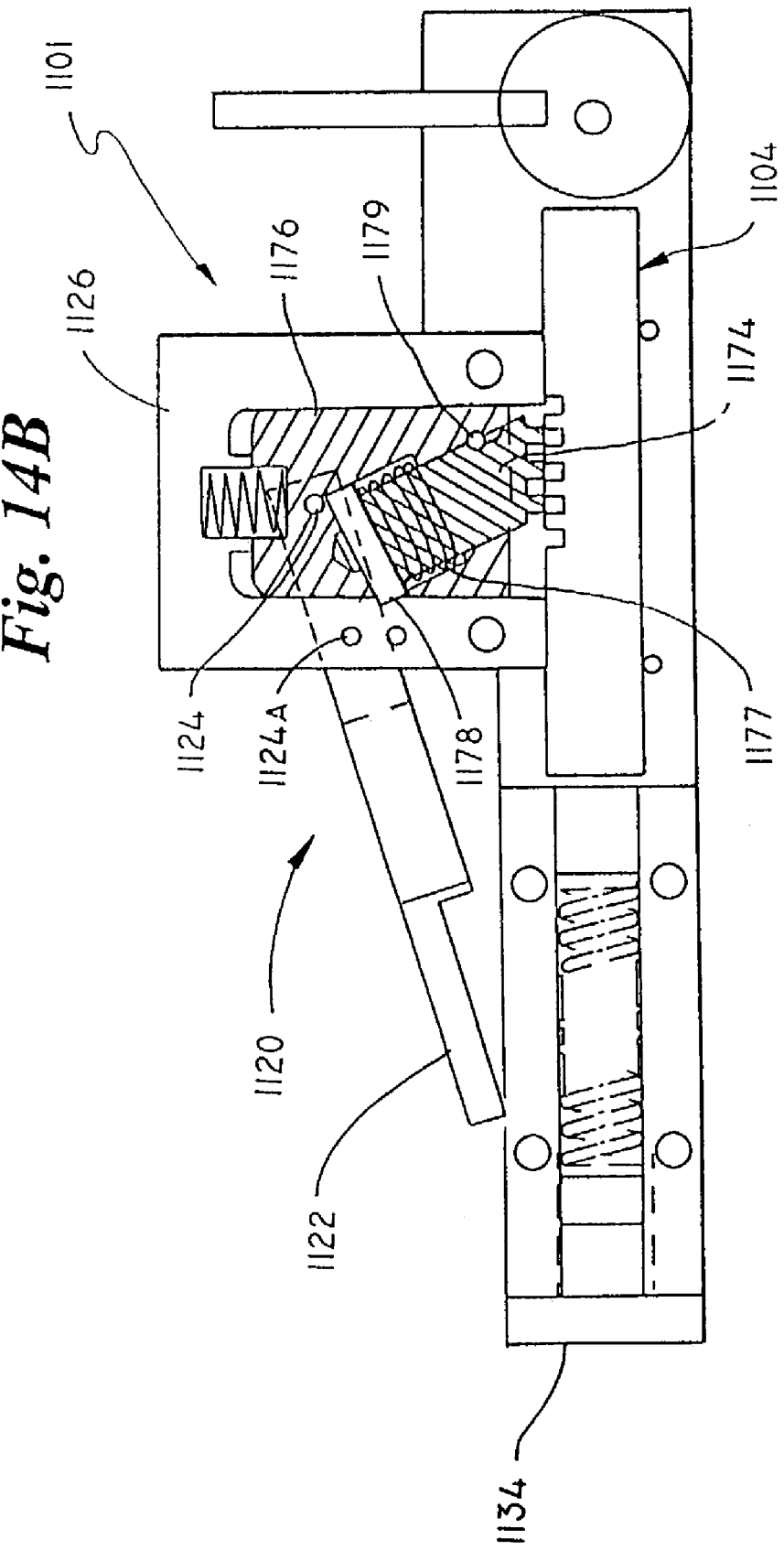

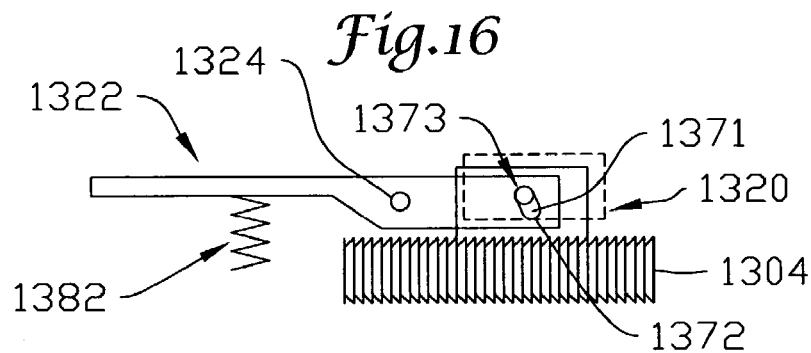
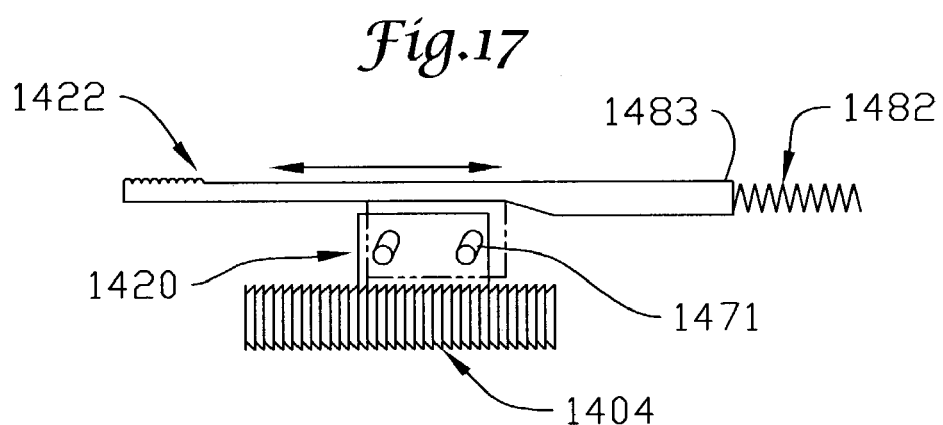
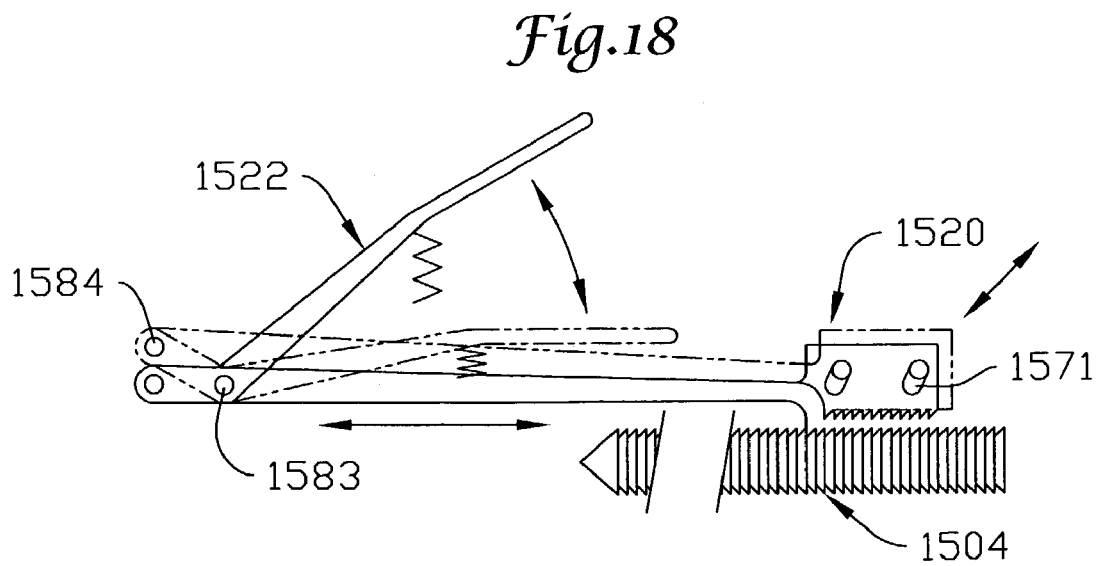

PRESSURE RELIEF DEVICES FOR USE WITH BALLOON CATHETERS

FIELD OF THE INVENTION

The present invention relates to pressure relief mechanisms for balloon catheters. More particularly, the present invention relates to mechanisms for relieving pressure within an inflation lumen and/or the balloon of a balloon angioplasty catheter.

BACKGROUND OF THE INVENTION

The use of balloon catheters for a variety of treatment procedures has risen greatly in recent years. Advancements in catheter procedures have led to more and more uses in different areas of the body for balloon catheters. Balloon catheters often require some sort of inflation device to create pressure for inflating a balloon once the catheter has been introduced into a patient's body and advanced to a proper location for inflation.

The inflation device coupled to a balloon catheter often functions as a modified syringe. A syringe is a device including a cylindrical chamber having openings on both ends; one opening is usually a small opening and the other is comparatively large. A plunger which slidably, yet sealingly fits the inner walls of the cylindrical chamber may be advanced from the larger opening toward the smaller opening to force a fluid through the smaller opening, and, oppositely, the plunger may be pulled from the smaller opening toward the larger opening to suck a fluid into the cylindrical chamber through the smaller opening. The plunger is usually attached to one end of a shaft with the other end of the shaft protruding out the larger opening of the syringe. Inflation devices for use with balloon catheters often modify the basic syringe just described by using a threaded shaft coupled to a threaded knob to advance and withdraw the plunger.

Occasionally during a procedure, a patient may begin to feel discomfort or pain due to the inflation of a catheter balloon. In some instances, the discomfort or pain may be an indicator of potentially serious problems with the procedure. For example, during a percutaneous transluminal coronary angioplasty, a patient's discomfort or pain may indicate initiation of tissue death due to lack of oxygen. In such a situation, it becomes desirable to quickly deflate the balloon to restore more normal body functions including, in some cases, normal blood flow and oxygenation. In other procedures, damage or tearing of tissue expanded by inflation of the balloon, the cutting off of fluid flow, or patient discomfort and pain may arise as a result of balloon inflation. In such situations, it would be desirable to have reliable devices for quickly reducing the pressure inside a catheter balloon.

One of the problems facing physicians is that, because many components used in catheter devices are relatively flexible metals or plastics, the threads holding the plunger in place in the inflation device at a high pressure may temporarily deform under strain, or may simply become more "sticky" due to friction between components at higher pressures, making it difficult to release pressure built up inside the balloon. Therefore, it is a goal of the present invention to provide a way to more quickly release pressure in a catheter balloon.

SUMMARY OF THE INVENTION

The present invention includes several embodiments of inflation devices incorporating elements for relieving pressure in a catheter balloon. In several of the embodiments, pressure relief mechanisms are provided for use with a modified syringe inflation device that may be coupled to a balloon catheter for inflating the balloon. The modified syringe inflation device may include a threaded shaft for advancing or withdrawing a plunger placed in slidable, yet sealing fit within a cylindrical chamber. In addition to the threaded shaft, the modified syringe inflation device may include an engagement mechanism that is threaded to engage the threading of the threaded shaft. The engagement mechanism may have two positions, a first in which it is engaged with the threaded shaft, and a second in which it is not. By twisting the engagement mechanism with respect to the threaded shaft (or, similarly, twisting the threaded shaft with respect to the engagement mechanism) while the engagement mechanism is engaged with the threaded shaft, the plunger may be forcibly advanced or withdrawn in the cylindrical chamber. In the second position, pressure is quickly relieved because the threads are disengaged, and the plunger may be quickly pulled back. The present invention generally relates to mechanisms for controlling whether the engagement mechanism is in the first, engaged, position or the second, disengaged, position, and further mechanisms or elements for more easily, quickly, or cleanly effecting changes in the position of the engagement mechanism.

Several embodiments include mechanisms for holding the engagement mechanism in the first, engaged, position until a doctor or other user decides to release the pressure by moving the engagement mechanism to the second position. Several embodiments further include mechanisms for enabling a doctor or other user to disengage the engagement mechanism while there is significant pressure in the cylindrical chamber. Some embodiments further include mechanisms for assuring that the step of disengaging the engagement mechanism does not damage the threads of the engagement mechanism or the threads of the threaded shaft.

In several embodiments, the engagement mechanism is designed to engage the threaded shaft for only a portion of the circumference of the threaded shaft. Thus, the engagement mechanism may be moved, without disassembly, away from the threaded shaft. Several engagement mechanisms could be used at once to achieve engagement of the threaded shaft around the entire circumference of the threaded shaft. In several embodiments, the engagement mechanism includes a shifting apparatus for shifting the engagement mechanism toward or away from the threaded shaft. The shifting apparatus may include an extension of the engagement mechanism, a lever, a spring, a gear, a link, combinations thereof, as described in representative embodiments in more detail below.

For example, the engagement mechanism may be connected to a moveable lever that can be moved about a pivot point. In an illustrative embodiment, the engagement mechanism is pressed against the threaded shaft by a spring when the lever is in a first location, while, when the lever is in a second location, the engagement mechanism is pulled away from the threaded shaft and disengaged. In another embodiment using a lever, a buckled collar is provided to hold the engagement mechanism in place and engaged with the threaded shaft; after the buckled collar is unbuckled and loosened, a lever may then be used to pull the engagement mechanism away from the threaded shaft and cause disengagement. Several alternative embodiments also include the use of a lever and are described in more detail below.

In other embodiments, the engagement mechanism is linked to a gear, the teeth of the gear having teeth matching and in contact with a track on the inside of a collar. In an illustrative embodiment, the engagement mechanism is pushed against the threaded shaft by a spring when the collar is in a first location, while, when the collar is in a second location, the gear turns about a stationary pin, pulling the link, and the engagement mechanism is thus pulled away from the threaded shaft and disengaged.

In several embodiments, a pop-away mechanism is also included for causing the engagement mechanism to pop away from the threaded shaft, protecting the threads of the threaded shaft and the engagement mechanism. Such a pop-away mechanism, in an illustrative embodiment, enables the engagement mechanism to pull away so that the distance between the central shaft of the threaded shaft and the recessed portion of the threads on the engagement mechanism is sufficient to ensure that, upon disengagement, the threads of the retracting threaded shaft and the threads of the engagement mechanism do not come into contact before complete disengagement is achieved.

In some illustrative embodiments, the pop-away mechanism includes a spring which connects a first portion of the engagement mechanism to a second portion of the engagement mechanism. In several embodiments, the first portion of the engagement mechanism is the portion to which a force pulling the engagement mechanism away from the threaded shaft is directly applied, and the second portion of the engagement mechanism is the portion that comes into contact with the threaded shaft. In an illustrative embodiment, as the first portion of the engagement mechanism is pulled away from the threaded shaft, the spring is stretched while forces between the threads of the engagement mechanism and the threaded shaft remain strong enough to prevent movement along the spring. In this illustrative embodiment, the spring is chosen so it will stretch a predetermined distance before sufficient force is applied to the spring to overcome the force holding the threads of the engagement mechanism to the threaded shaft. Once the force applied to the spring is sufficient, the second portion of the engagement mechanism springs away from the threaded shaft, pulling back a sufficient distance to assure complete disengagement.

BRIEF DESCRIPTION OF THE DRAWINGS

FIG. 1 is a plan view of a balloon catheter which may be used in conjunction with the present invention;

FIG. 3 is a cross-sectional view through line 3—3 of FIG. 2;

FIG. 14B is an alternative plan view of the pressure relief mechanism shown in FIG. 14;

FIG. 16 is a plan view of an illustrative embodiment of a pressure relief mechanism in accordance with the present invention;

FIG. 17 is a plan view of an illustrative embodiment of a pressure relief mechanism in accordance with the present invention; and FIG. 18 is a plan view of an illustrative embodiment of a pressure relief mechanism in accordance with the present invention.

DETAILED DESCRIPTION OF THE DRAWINGS

Figure 2:
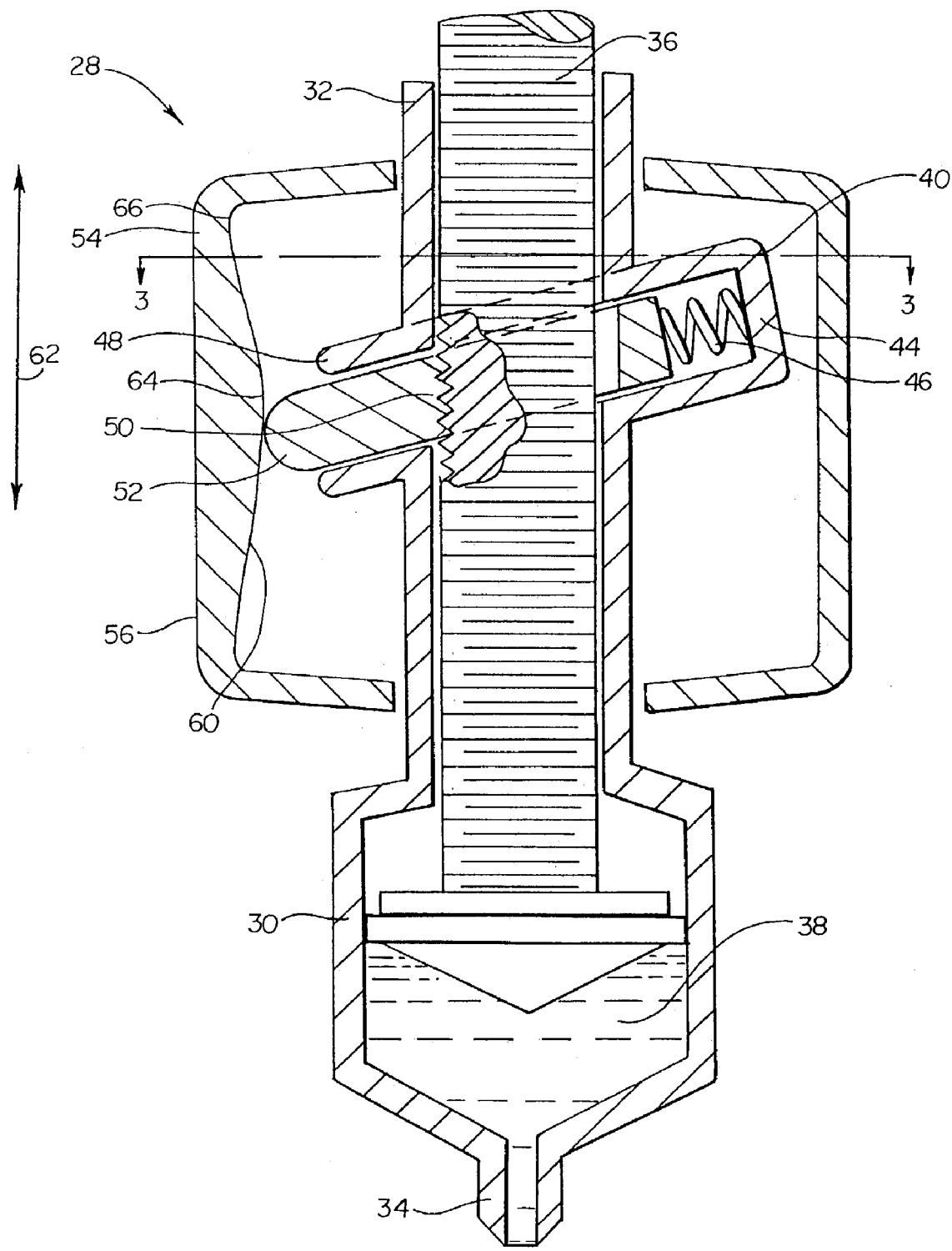
FIG. 2 is a plan view with partial cut away views of an illustrative embodiment of a pressure relief mechanism in accordance with the present invention.

The following detailed description should be read with reference to the drawings wherein like reference numerals indicate like elements throughout the several views. The detailed description and drawings illustrate exemplary embodiments of the claimed invention.

FIG. 1 is a plan view of a balloon catheter 10. Balloon catheter 10 includes an elongate member 12 having a proximal end 14 and a distal end 16. Included near distal end 16 is balloon 18. Balloon 18 is in fluid communication with a lumen 26, which is in turn in fluid communication with port 27 including coupling 28. Coupling 28 may attach to a syringe or other inflation device, placing the outlet of the syringe in fluid communication with the lumen 26.

A pressure release mechanism may be incorporated into or attached to the syringe or other inflation device so that when balloon 18 is inflated, the pressure inflating the balloon 18 may be quickly released to deflate balloon 18 in circumstances presenting a need for such a quick pressure release. One example of such a situation could be during a percutaneous transluminal coronary angioplasty (PTCA) procedure, in which the balloon 18 may be inflated within a blood vessel, preventing blood flow in the vessel. After a time, certain tissue that would ordinarily receive blood and oxygen supply from the blocked vessel, without the balloon 18 in place and inflated, may begin to experience oxygen starvation, and the patient in whom the procedure is taking place may exhibit symptoms. On such an occasion, it may be necessary to quickly release pressure inside the balloon. However, pressures inside the syringe, lumen 26 and balloon 18 may be sufficiently high to render quick release more difficult. Therefore, a pressure release mechanism is included in preferred embodiments of the syringe or inflation device.

FIG. 2 is a plan view with a partial cut out region of an illustrative embodiment of the present invention. Pressure release mechanism 28 includes a plunger 30 for a syringe or other inflation device disposed within a cylinder wall 32 of the syringe or other inflation device or other inflation device. A threaded shaft 36 connects to plunger 30. An interface between the threaded shaft 36 and the plunger 30 may enable the threaded shaft 36 to be rotated without requiring plunger 30 to also rotate in some embodiments. Between plunger 30 and outlet 34 is an inflation media 38. Various materials are known for use in balloon catheters as inflation media including, for example, saline solutions or other inflation fluids. In many embodiments, the outlet may be coupled to a balloon catheter such as the one shown in FIG. 1, and outlet 34 may be coupled via coupling 29 to a port 27 in FIG. 1.

As plunger 30 is advanced toward outlet 34, inflation media 38 is forced out of the outlet 34. If outlet 34 is coupled to a port of a balloon catheter and in fluid communication with a balloon via an inflation lumen, inflation media 38 will be forced into the balloon. As the balloon fills, pressure will build in the balloon, the connecting or inflation lumen, and between the plunger 30 and outlet 34. In some medical procedures using a balloon catheter, the balloon will be filled until it reaches a specified diameter or until internal pressure reaches a specified level. If the plunger is drawn away from outlet 34, inflation media 38 will be sucked back into the volume between plunger 30 and outlet 34, reducing pressure or creating suction past outlet 34. In several illustrative embodiments of the present invention, the plunger 30 is advanced or drawn back by twisting the threaded shaft 36 against an engagement mechanism so that the longitudinal spacing of the threads on the shaft 36 guide movement of the shaft 36 that is parallel with the central axis of the shaft 36 in one stage, while in another stage, the plunger may be advanced or drawn back by simply pulling or pushing on the threaded shaft 36.

In the illustrative embodiment shown in FIG. 2, an engagement mechanism 50 protrudes from an opening 48 in the cylinder 32. The engagement mechanism 50 may include threads or other projections that mesh with the threads on the threaded shaft 36. Some illustrative threads or other projections on engagement mechanisms for use with several embodiments of the present invention are shown in FIGS. 9A, 9B, 10A, and 10B. However, those illustrative engagement mechanism threads or projections do not comprise an exhaustive list. Any mechanism or apparatus capable of matching, meshing with, or interfacing a threaded shaft, where the threaded shaft may be either a helically threaded shaft or may include a series of adjacent rings, may be equivalent.

Further, the threaded shaft may be of various types, for example cylindrically shaped, conical, or discontinuous cylinders wherein, selecting a point on the central axis of the shaft, threads may appear in certain parts of the area around the shaft, and other areas of the shaft may be smooth, cut in, or cut out. The threads themselves may vary as well, for example, having a continuous outer rim versus jagged or toothed outer rims, and may have outer rims which are sharp or come to a point or, instead, may come to a rounded, square, or other polygonal shaped end. Various types of threaded shafts are known throughout the mechanical arts, many of which will function equally well in various embodiments of the present invention.

In the illustrative embodiment of FIG. 2, the engagement mechanism 50 is connected to an extension 52 and a spring 46. The spring 46 is shown placed inside a recess 44 in the cylinder 32. A collar 54 is shown surrounding and encapsulating the engagement mechanism 50 and the recess 44. The inner wall 60 of the collar 54 is not flat with respect to the cylinder; it instead has a reduced radius in one location 64 and a larger radius in another location 66.

For the illustrative embodiment in FIG. 2, the collar 54 may slide back and forth as indicated by arrows 62. When, as is shown in FIG. 2, the collar 54 is in a first location, the extension contacts the inner wall 60 of the collar 54 at a location 64 with a reduced radius, so that the engagement mechanism 50 is pressed against the threaded shaft 36, causing the threads of the engagement mechanism 50 and the threaded shaft 36 to engage. When the threads of the engagement mechanism 50 and the threaded shaft 36 are engaged, advancement or withdrawal of the plunger 30 will require twisting of the threaded shaft; for purposes of this specification, this will be the definition of "engaged". When the collar 54 is in another location, so that extension 50 strikes the inner wall 60 of the collar 54 at a location 66 having a larger radius, the spring 46 is biased to push the engagement mechanism 50 away from threaded shaft 36, disengaging the threads of the engagement mechanism 50 and threaded shaft 36. When the threads of the threaded shaft 36 and the engagement mechanism 50 are disengaged, the plunger 30 may be advanced or withdrawn by pushing or pulling on the threaded shaft 36, without needing to twist the shaft 36; for the purposes of this specification, this will be the definition of "disengaged".

FIG. 3 is a cross-sectional view of an illustrative embodiment taken approximately through line 3—3 of FIG. 2. In FIG. 3, a threaded shaft 80 is shown with the engagement mechanisms having two possible positions 90, 94. When in a first position 90 (solid line), the engagement mechanism and shaft 80 are disengaged, and when in a second position 94 (dashed line), the engagement mechanism and shaft 80 are engaged, as shown by contact at a location 96. In the illustrative embodiment of FIG. 3, spring 86 is set inside recess 88 in the syringe cylinder wall. The spring 86 pushes the engagement mechanism against the inner wall 82, 84 of the collar 81. When the collar 81 is in a first position, the inner wall 82 against which extension 92 presses has a larger radius (distance from inner wall 82 to shaft 80) than when collar 81 is in a second position when extension 96 presses against inner wall 84 (distance from inner wall 84 to shaft 80). Because the radius of the inner wall of the collar 81 has changed from a larger radius 82 to a smaller radius 84, the position of the engagement mechanism has changed from a first position 90 to second position 94.

Figure 4:
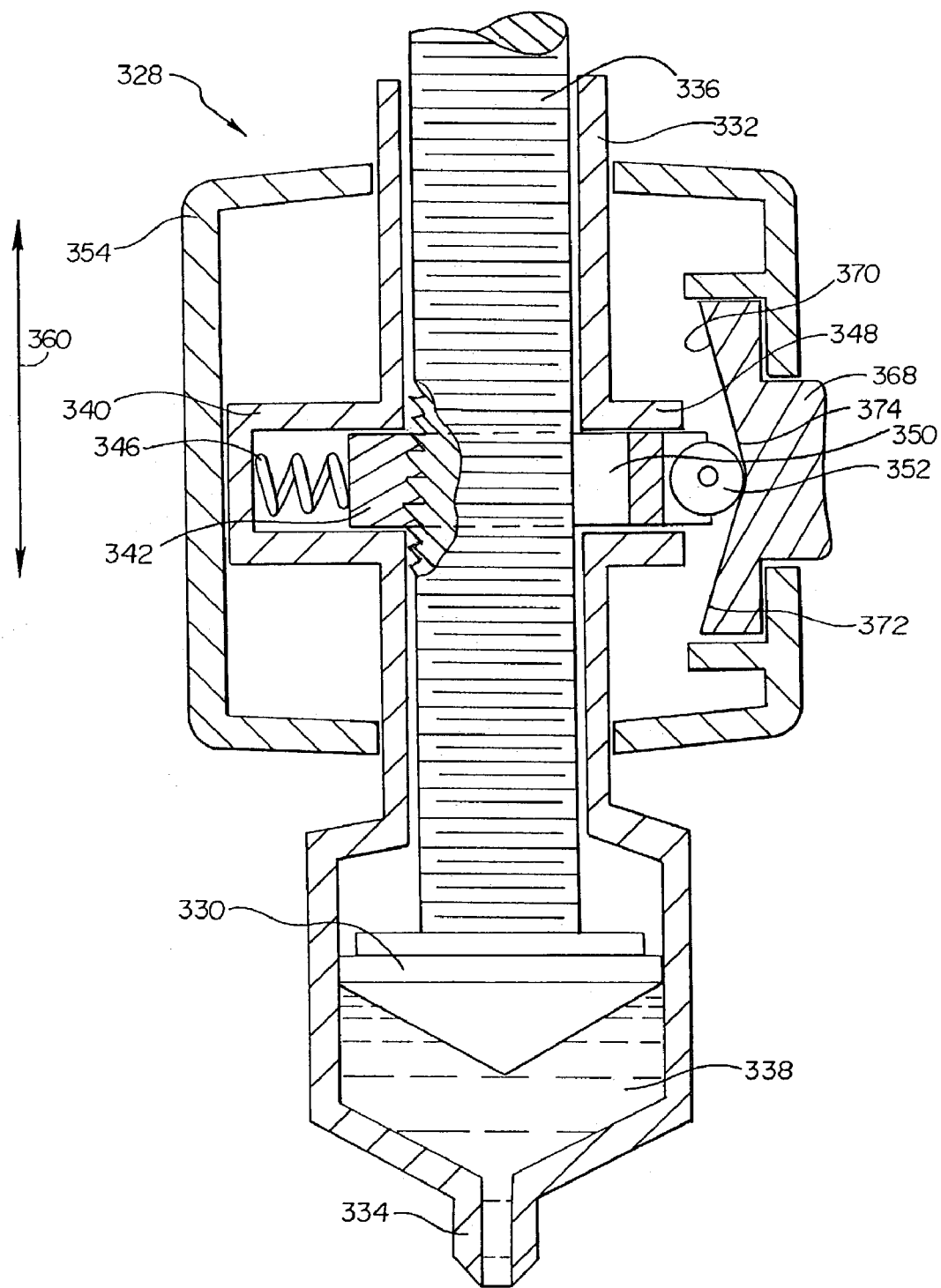
FIG. 4 is a plan view with partial cut away views of an illustrative embodiment of a pressure relief mechanism in accordance with the present invention.

FIG. 4 is a plan view with a partial cut away section of another illustrative embodiment of the present invention. Pressure release mechanism 328 includes plunger 330 disposed within cylinder 332 having outlet 334. Between the plunger 330 and outlet 334 is inflation media 338, and threaded shaft 336 is attached on the opposing side of plunger 330.

Engagement mechanism 342 is disposed within a recess 340 of the wall of cylinder 332 along with a spring 346, which is biased to press the engagement mechanism 342 toward the threaded shaft 336. An opening 348 in the cylinder 332 opposes the recess 340. Extension 350 is connected to engagement mechanism 342 and comes into contact with a button 368 through opening 348. The button 368 is incorporated into a collar 354 that surrounds the area of the cylinder 332 where the recess 340 and opening 348 are. The collar 354 may slide as indicated by arrows 360. The inner wall 370 of the button 368 includes an area of greater radius 374 and an area of lesser radius 372. The point of contact between the extension 350 and the button 368 may include a contact wheel 352, which may facilitate easier movement of the collar 354 in the directions shown by the arrows 360.

When the point of contact between the extension 350 and the button 368 occurs at an area of the inner wall 370 corresponding to a greater radius 374 (as shown in FIG. 4), the spring 346 presses the engagement mechanism 342 against the threaded shaft 336, causing the engagement mechanism 342 and threaded shaft 336 to engage. However, if the button 368 is depressed, the button 368 will press against the extension 350 against the bias of the spring 346, moving the engagement mechanism 342 away from the threaded shaft 336 and disengaging the engagement mechanism 342 and threaded shaft 336.

Also, in the illustrative embodiment of FIG. 4, if the collar 354 is moved so that the point of contact between the extension 350 and the button 368 occurs at an area of the inner wall 370 corresponding to a lesser radius 372, the button 368 will press the extension 350 against the bias of the spring 346, likewise disengaging the engagement mechanism 342 and threaded shaft 336. Thus, the illustrative embodiment of FIG. 4 shows two ways for disengaging the engagement mechanism 342 and threaded shaft 336. It is contemplated that, for the illustrative embodiment of FIG. 4, the button 368 could be depressed to disengage when a lower pressure is present in the inflation media 338, while the collar 354 could be slid to disengage when a higher pressure is present in the inflation media 338.

Figure 5:
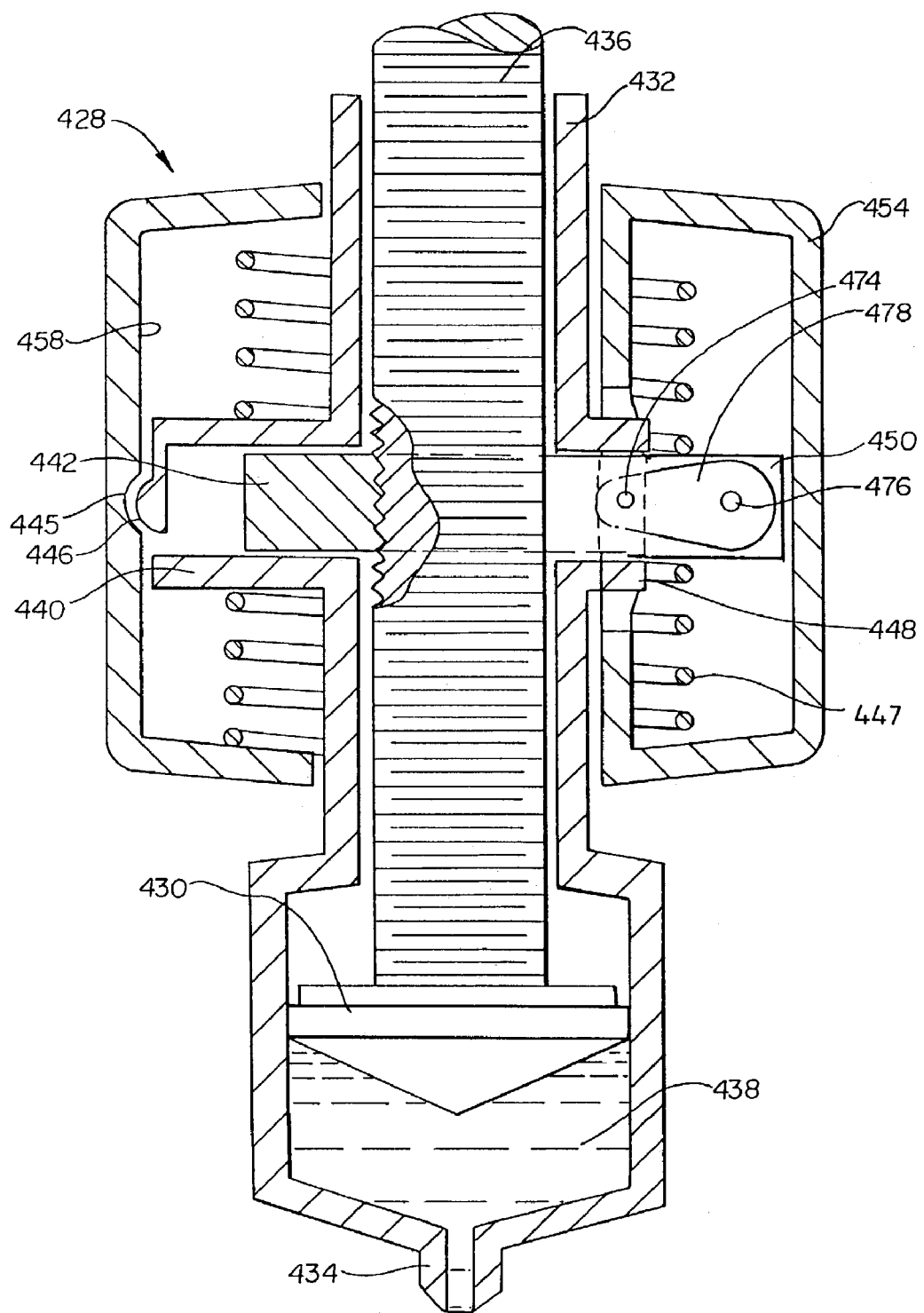
FIG. 5 is a plan view with partial cut away views of an illustrative embodiment of a pressure relief mechanism in accordance with the present invention.

FIG. 5 is a plan view with partial cut away views of an illustrative embodiment of a pressure relief mechanism in accordance with the present invention. Pressure release mechanism 428 includes plunger 430 disposed within cylinder 432 having outlet 434. Between the plunger 430 and outlet 434 is inflation media 438, and threaded shaft 436 is attached on the opposing side of plunger 430.

An engagement mechanism 442 is disposed within a first opening 440 of cylinder 432. An extension 450 that projects through a second opening 448 in the cylinder 432 is connected to the engagement mechanism 442 and controls the position of the engagement mechanism 442. The first opening 440 and the second opening 448 may be connected to form a single opening in some embodiments. A link 478 is attached to the extension 450 with a pin 476, and is also attached to a collar 454 with a second pin 474. The collar 454 is connected to a spring 447 that may exert a net force between the collar 454 and the opening(s) 440, 448 when the spring 447 is not in an equilibrium position. The inner wall 458 of the collar 454 may include a notch 445 corresponding to a protrusion 446 from the cylinder 432. The specific placement of the protrusion 446 may vary, for example, the collar 454 may include a second protrusion that extends away from the location of the engagement mechanism 442, which can correspond to the protrusion 446, and several protrusions 446 may be used in the same embodiment.

The link 478 is adapted to move when the collar 454 moves. In the illustrative embodiment of FIG. 5, when the collar 454 is in a first location where the spring 447 is approximately in equilibrium, the link 478 pushes the extension 450 causing the engagement mechanism 442 to engage the threaded shaft 436. The protrusion 446 and corresponding notch on the inner wall 458 are placed so that the protrusion 446 may extend into the notch 445 when the spring 447 is approximately in equilibrium and the engagement mechanism 442 and threaded shaft 436 are engaged. It is conceived that the mating of notch 445 and protrusion 446 along with the equilibrium position of the spring 447 will combine to maintain the engagement of the engagement mechanism 442 and threaded shaft 436.

Also in the illustrative embodiment of FIG. 5, the collar 454 may slide with respect to the openings 440, 448, pressing against the net force of the spring 447 and moving the protrusion 446 away from the notch 445. As the collar 454 slides, the link 478 is pulled into a different angle, causing the extension 450 to move, in turn moving the engagement mechanism 442 away from the threaded shaft 436 and causing disengagement.

Figure 6:
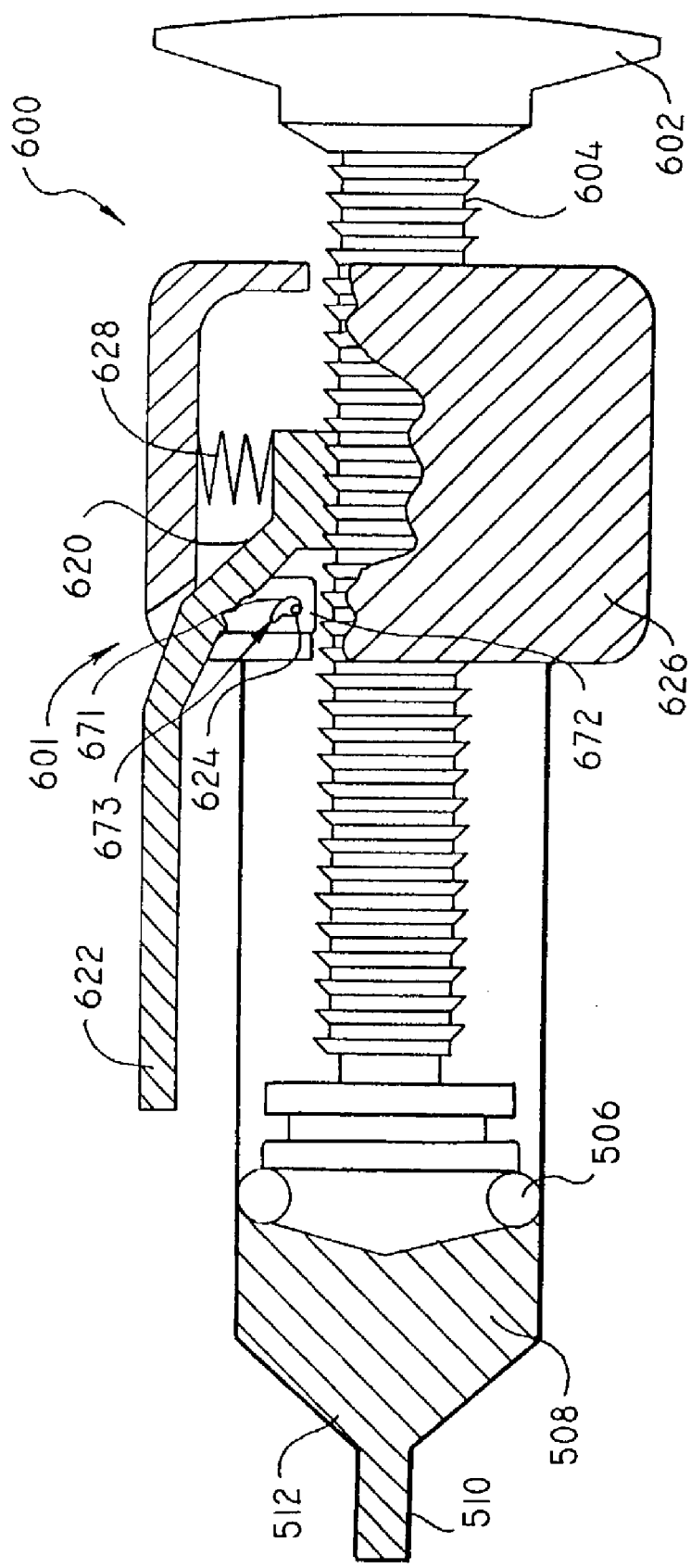
FIG. 6 is a plan view of an illustrative embodiment of a pressure relief mechanism in accordance with the present invention.
Figure 7A:
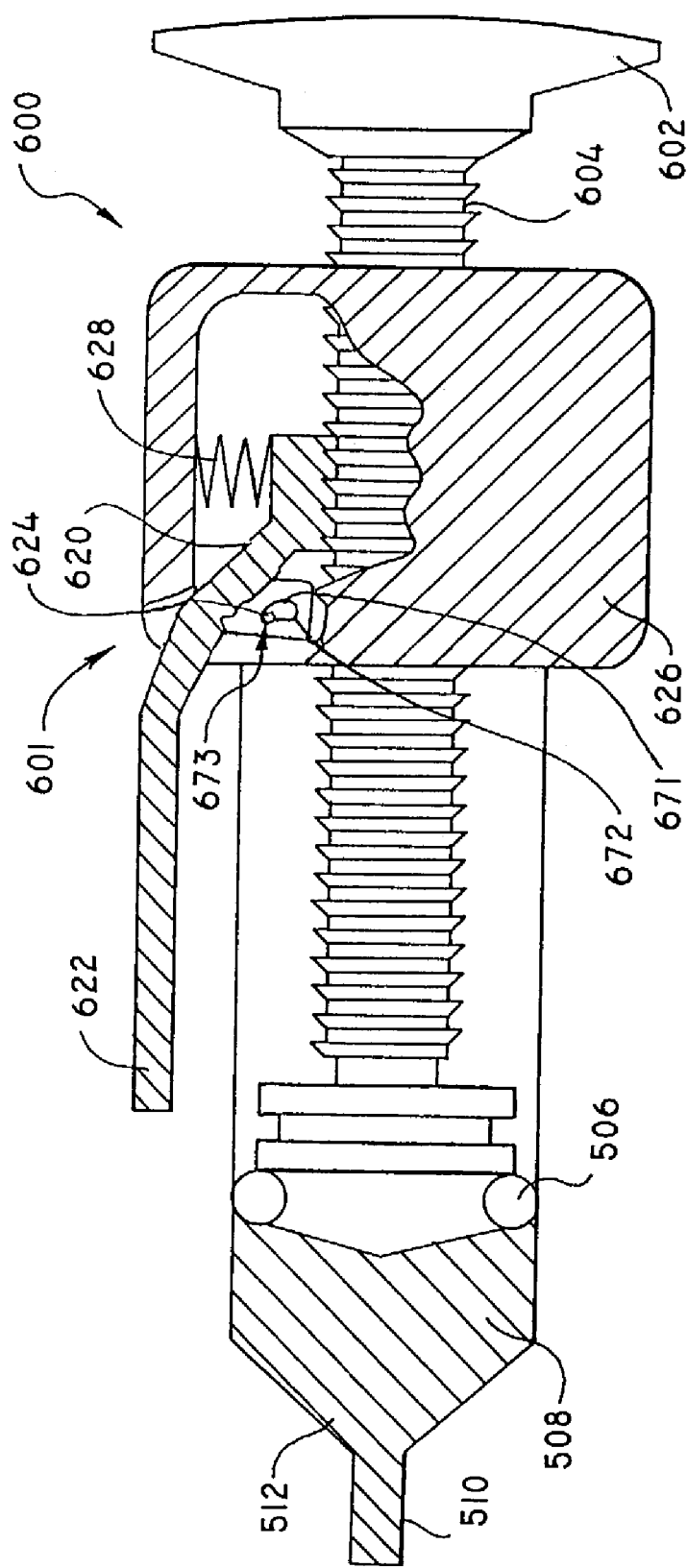
FIG. 7A is an alternative plan view of the pressure relief mechanism shown in FIG. 6.

FIG. 6 depicts an alternative pressure relief mechanism 601 including knob 602, plunger 604, engagement mechanism 620, lever 622, pin 624, collar 626, and one or more springs 628 to hold engagement mechanism 620 in the first position. Pressure relief mechanism 601 is essentially the same in form and function as mechanism 501 except that lever 622 includes an opening 671 with a first notch 672 and a second notch 673 located distal to first notch 672. By including opening 671, partially or completely depressing lever 622 can result in pin 624 shifting between first notch 672 and second notch 673. For example, pin 624 may move from first notch 672 to second notch 673 when lever 622 is partially actuated as shown in FIG. 7A.

Figure 7B:
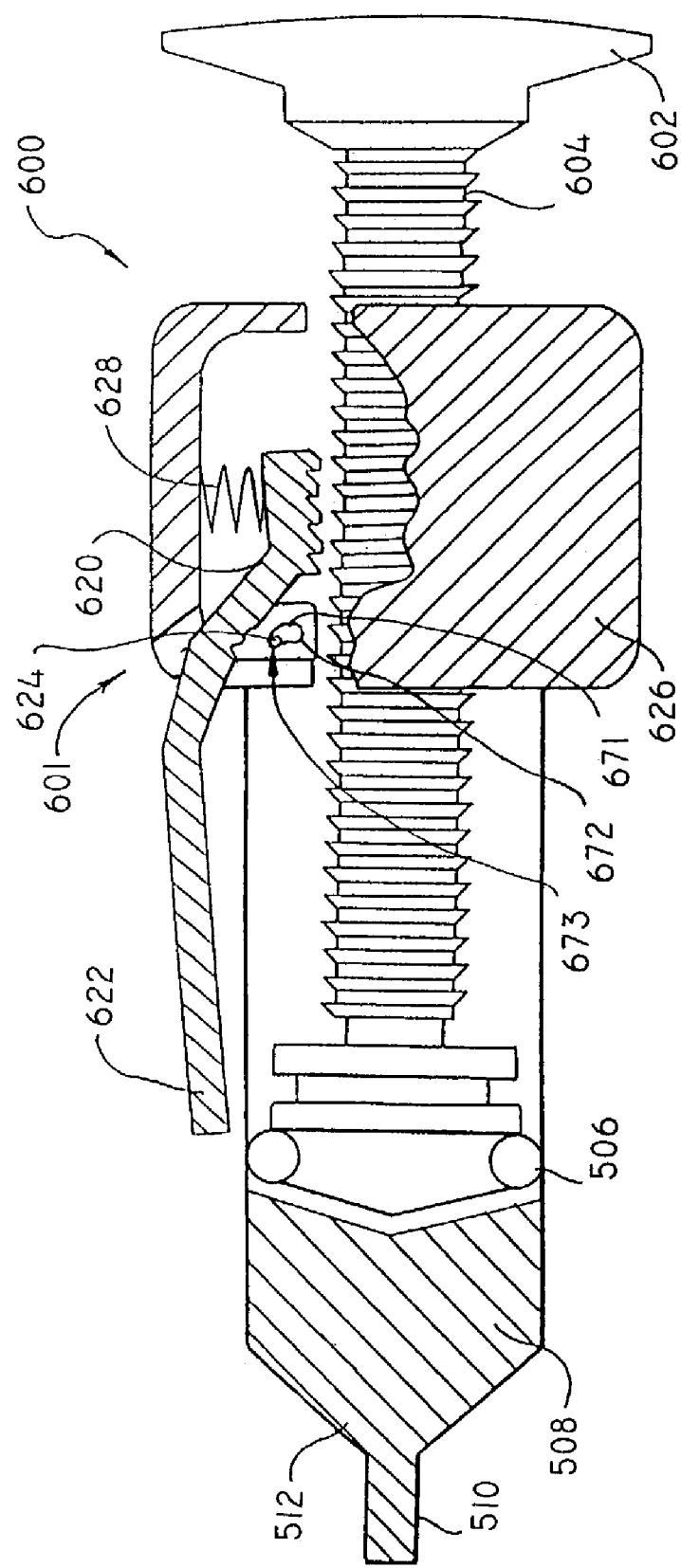
FIG. 7B is an alternative plan view of the pressure relief mechanism shown in FIG. 6.

The result of this shift may be the proximal movement of both engagement mechanism 622 and the plunger 604. By proximally shifting plunger 604 a relatively short distance (e.g., the distance between first notch 672 and second notch 673), fluid pressure exerted on plunger 604 will be reduced sufficiently so that plunger 604 may be easily turned or unscrewed by knob 602. Moreover, depressing lever 622 completely to a second position may overcome the bias of spring 628 and result in engagement mechanism 620 disengaging from plunger 604 as shown in FIG. 7B.

Figure 8:
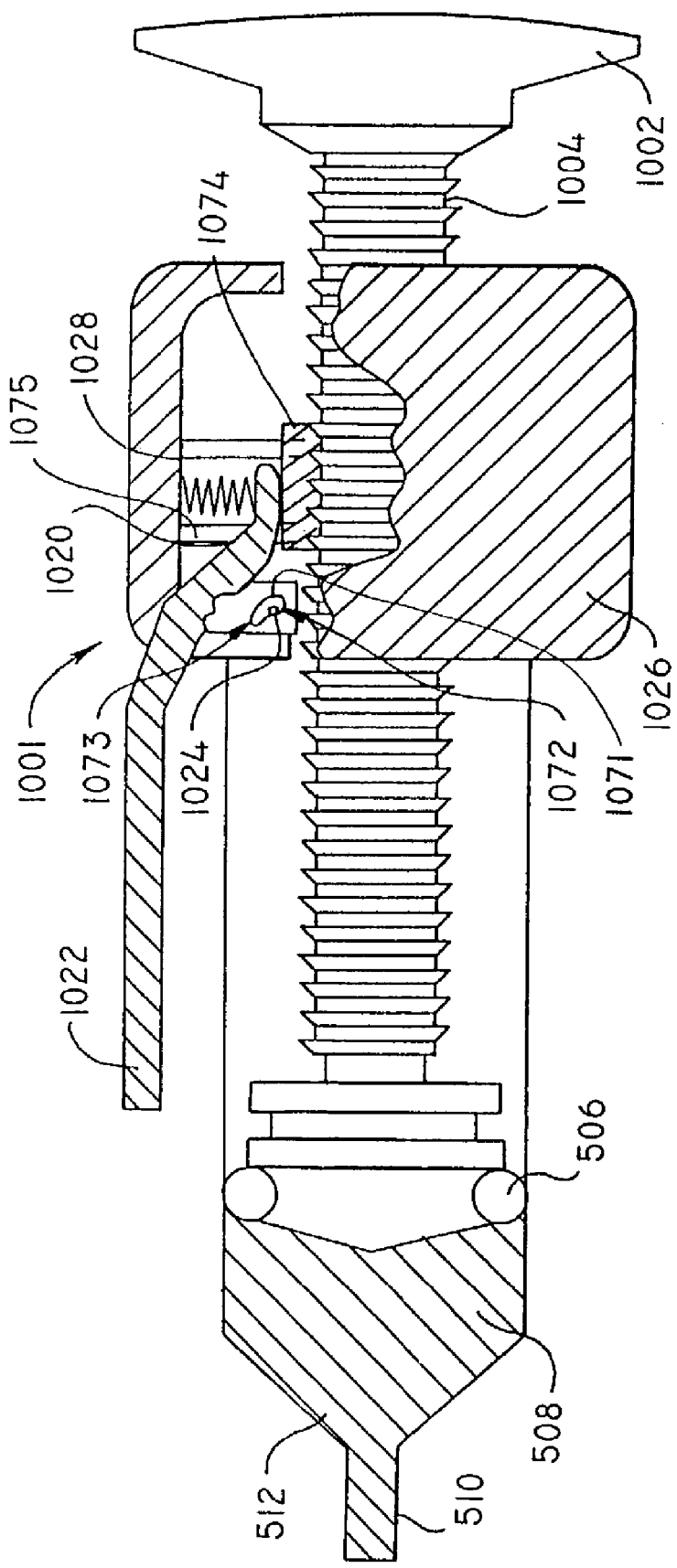
FIG. 8 is a plan view of an illustrative embodiment of a pressure relief mechanism in accordance with the present invention.

FIG. 8 is an alternative pressure relief mechanism 1001 including knob 1002, plunger 1004, engagement mechanism 1020, lever 1022, pin 1024, collar 1026, and one or more springs 1028 to hold engagement mechanism 1020 in the first position. Similarly to what is described above, lever 1022 includes an opening 1071 with a first notch 1072 and a second notch 1073 that functions analogously to 622 (and opening 671). According to the embodiment illustrated in FIG. 8, engagement mechanism 1020 includes a nut 1074 adapted and configured to threadably engage plunger 1004. Opposite ends of spring 1028 are coupled to collar 1026 and nut 1074. Spring 1028 is biased to exert force on nut 1074 sufficient to press it toward plunger 1004.

Lever 1022 is coupled to nut 1074, for example by a spring. One or more rails 1075 may be disposed between lever 1022 and nut 1074 to maintain the longitudinal position of the nut 1074 relative to lever 1022. Partially or completely depressing lever 1022 may shift pin 1024 from first notch 1072 to second notch 1073. This shift will result in an analogous shift of plunger 1004 as described above. Moreover, because spring 1028 is biased to press nut 1074 toward plunger 1004, it will help keep nut 1074 and plunger 1004 engaged during the proximal shift of position of plunger 1004. Additional or complete depressing of lever 1022 will exert additional force on nut 1074 sufficient to overcome the bias of spring 1028 and result in nut 1074 disengaging from plunger 1004.

Figure 9A:
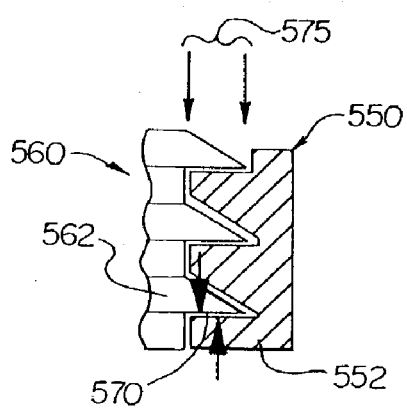
FIGS. 9A–9C are enlarged views of threads of an illustrative embodiment of a syringe used to illustrate a potential difficulty.
Figure 9B:
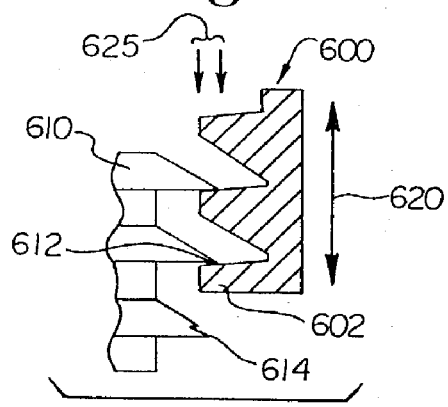
Figure 9C:
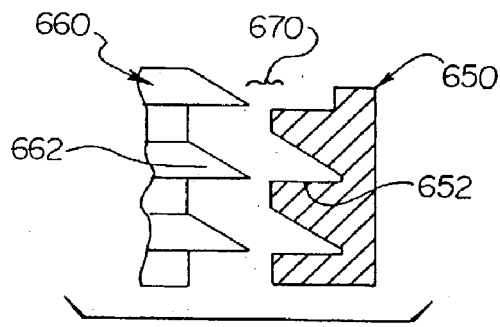

FIGS. 9A–9C are enlarged views of threads in an engaged position, a ratcheting position, and a disengaged position. FIG. 9A shows a threaded shaft 560 having threads 562 and an engagement mechanism 550 having engaging threads 552. As shown, there is a depth of engagement 575 in which the threads and engaging threads overlap. When forces are exerted in opposing directions on the threaded shaft 560 and the engagement mechanism 550, individual threads 562 and engaging threads 552 are in contact 570. If a force is exerted to move the threaded shaft 560 away from the engagement mechanism 550, it must overcome a frictional force (both static and moving) that occurs due to the contact 570. Further, with respect to catheter devices in general, many components are made of relatively flexible materials and plastics, which may deform and further add to the friction at contact 570.

FIG. 9B shows a problem which may arise as a threaded shaft 610 and an engagement mechanism 600 are being separated. The threaded shaft 610 and engagement mechanism 600 have moved some distance away, but the distance is less than the depth of engagement 570 (shown in FIG. 9A), so that the individual threads 612 and engagement threads 602 continue to overlap. If a force is applied in a direction parallel 620 to the threaded shaft 610, the individual threads 612 or engagement threads 602 may bend or break 614 under the force. The bending and breaking 614 may occur due to forces applied in the parallel direction 620, which may be easily within stress and strain limitations of the individual threads 612 and engagement threads 602 at larger depths of engagement 575 (FIG. 9A), but fall outside the capacities of the threads 612 and engagement threads 602 at lesser depths of engagement 625. Thus, because the threaded shaft 610 and engagement mechanism 600 do not move far enough away during disengagement, damage, such as breaking of individual threads 614, may occur.

FIG. 9C shows complete disengagement of an engagement mechanism 650 from a threaded shaft 660. Individual threads 662 and engaging threads 652 are undamaged. A slight separation 670 exists. The separation 670 may be very small, and in fact can be virtually no distance at all for well made components. The threaded shaft 660 may freely move with respect to the engagement mechanism 650.

Figure 10A:
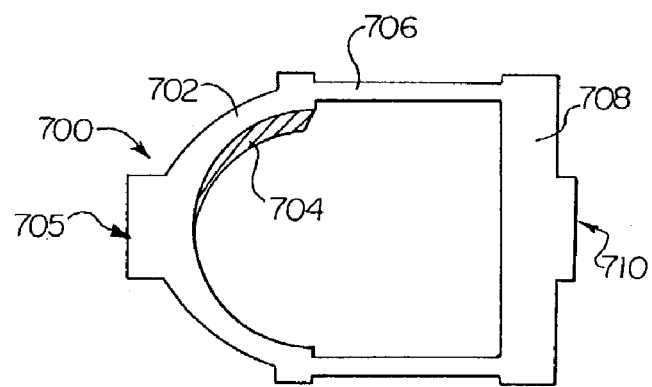
FIGS. 10A–10C are perspective views of thread engagement apparatus designed to overcome the problem illustrated in FIGS. 9A–9C.
Figure 10B:
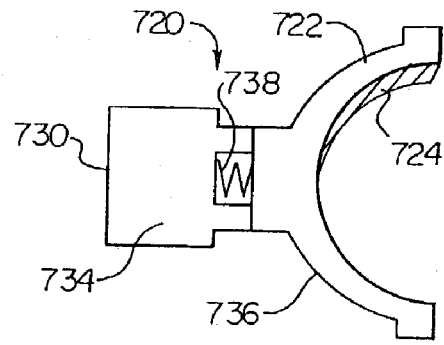
Figure 10C:
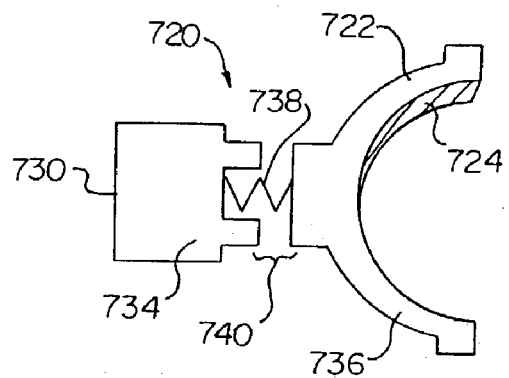

FIGS. 10A–10C are perspective views of thread engagement apparatus designed to overcome the problem illustrated in FIGS. 9A–9C. FIG. 10A shows a basic engagement apparatus 700. The engagement apparatus has a threaded section 702 having threads 704 for engaging a threaded shaft. A contact region 705 is shown connected to the threaded section 702. An extension 706 may extend out in a manner that avoids the threaded shaft, ending in a second section 708 including a second contact region 710. In several embodiments, the extension 706, second section 708 and second contact region 710 may be omitted. Upon application of a sufficiently large force to either contact region 705, 710 moving the threaded section 702 away from a threaded shaft, the engagement apparatus 700 will move in an approximately linear fashion. The linear motion may leave the threads 704 vulnerable to damage like the damage shown in FIG. 9B.

FIG. 10B shows an improved engagement apparatus 720 that may avoid or reduce exposure to damage like the damage shown in FIG. 9B. Engagement apparatus 720 includes a threaded section 722 having threads 724. A contact area 730 is connected, though the contact area 730 is in several other embodiments not precisely defined or included. The engagement apparatus 720 is divided into a first section 734 and a second section 736, which are connected to one another by an elastic section 738. In the embodiment shown in FIGS. 10B and 10C, the elastic section 738 is shown as a spring, and for convenience a spring is shown throughout these drawings. However, other elastic sections are also contemplated, including elastic bands, and elastomeric or elastic materials, for example. Any material that can be deformed and return to an approximate of an original shape will function.

FIG. 10C shows the improved engagement apparatus 720 as a force is applied to the first section 734 while an opposing force, for example, the frictional force between threads and engaging threads as shown in FIG. 9A, pulls on the second section 736. The elastic section 738 stretches in accordance with the elastic properties of the elastic section. Such elastic properties often provide a relationship between a distance of displacement or stretch and the force applied. For example, a spring may have a spring constant k, where the formula F=kx (also known as Hooke's law) applies, meaning that the magnitude of a pulling force (F) applied to a spring will equal the spring constant (k) times the distance the spring stretches (x). Other elastic materials and structures may be used, to which other formulae may apply, but the principle of an elastic material will remain the same: the amount of stretch exhibited by the material will increase as the pulling force applied to the material increases.

In the illustrative embodiment of FIG. 10C, as the pulling force increases, the amount of stretch exhibited by the elastic section 738 will increase as well. However, the amount of frictional force applied to the second section 736 at the threads 724 is finite, so as the force pulling force increases, eventually, the pulling force becomes sufficient to remove the second section from a threaded shaft, and the engagement apparatus 720 releases and disengages from the threaded shaft. The elastic section 738 may, in some embodiments, be selected to assure that a certain amount of stretching will occur under a given amount of friction before the engagement apparatus releases. The amount of stretching may be chosen to ensure that damage to the threads, as shown in FIG. 9B, does not occur. The amount of stretch may be chosen to exceed the depth of engagement that the engagement apparatus 720 and threaded shaft are anticipated to have.

It is also considered that forces other than frictional force may hold the second section 736 to the threaded shaft. For example, adhesive forces, magnetic forces, electric forces, and suction forces may also hold the second section 736 to the threaded shaft. It may be that, in some applications and embodiments, a magnetic force may be applied that can be chosen to render the frictional force of negligible importance, so that consistent operation of the release mechanism may be ensured.

Figure 11:
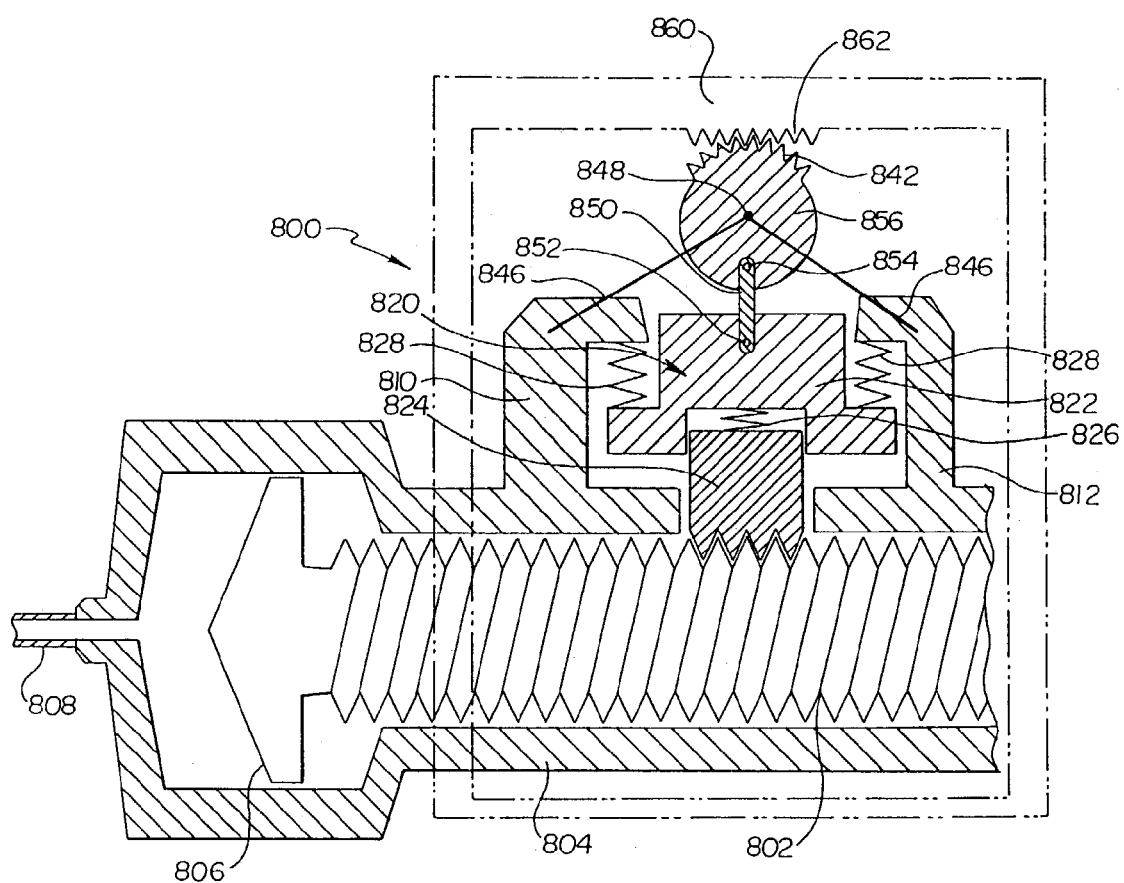
FIG. 11 is a plan view with partial cut away views of an illustrative embodiment of a pressure relief mechanism in accordance with the present invention incorporating the improvements of FIGS. 10B–10C.

FIG. 11 is a plan view with partial cut away views of an illustrative embodiment of a pressure relief mechanism in accordance with the present invention incorporating the improvements of FIGS. 10B–10C. In FIG. 11, pressure relief mechanism 800 includes a threaded shaft 802 within cylinder wall 804, the threaded shaft 802 being connected to a plunger 806, and the cylinder 804 ending on one end in an outlet 808. There is an opening in the cylinder 804 between outcroppings 810,812. An engagement mechanism 820 is disposed between the outcroppings 810,812. Engagement mechanism 820 includes a first part 822, a second part 824, and an elastic portion 826, the elastic portion 826 being shown as a spring, though other forms of the elastic portion 826 would be equivalent.

Springs 828 are biased to push the engagement mechanism 820 toward the threaded shaft 802. The engagement mechanism is also connected to a link 850 by a pin 852. The link 850 is connected by another pin 854 to a gear 856. The gear 856 is adapted to rotate about an axis 848 which is fixed to outcroppings 810,812 by supports 846. Gear 856 includes gear teeth 842. An outer collar 860 is also provided, and on a part of the outer collar 860 inner wall there are provided collar teeth 862 which correspond to, and can engage the gear teeth 842.

The illustrative embodiment of FIG. 11 functions by sliding the collar 860 back and forth to engage and disengage the engagement mechanism 820 and threaded shaft 802. When the collar is in a first location 860, the collar teeth 862 cause the gear teeth 842 to adopt a first position, causing the gear 856 to be aligned in the manner shown in FIG. 11. Thus, when the gear teeth are in the first position, the pin 854 connecting the link 850 to the gear 856 allows the link to be in a position nearer the threaded shaft 802, which in turn enables the engagement mechanism 820 to succumb to the bias of the springs 828 and engage the threaded shaft 802. When the collar 860 is in a second location, the collar teeth 862 cause movement of the gear teeth 842, and hence turn the gear 856. As the gear 856 turns about pivot 848, link 850 is pulled away from threaded shaft 802, applying a pulling force to the engagement mechanism 820. As the pulling force applied to the engagement mechanism 820 is applied, elastic portion 826 stretches until the force across the elastic portion 826 is sufficient to overcome the force holding the second part 824 to the threaded shaft 802, and the second part 824 snaps away from the threaded shaft 802, protecting threads on the second part 824 and the threaded shaft 802 as the engagement mechanism 820 and threaded shaft 802 become disengaged.

Figure 12:
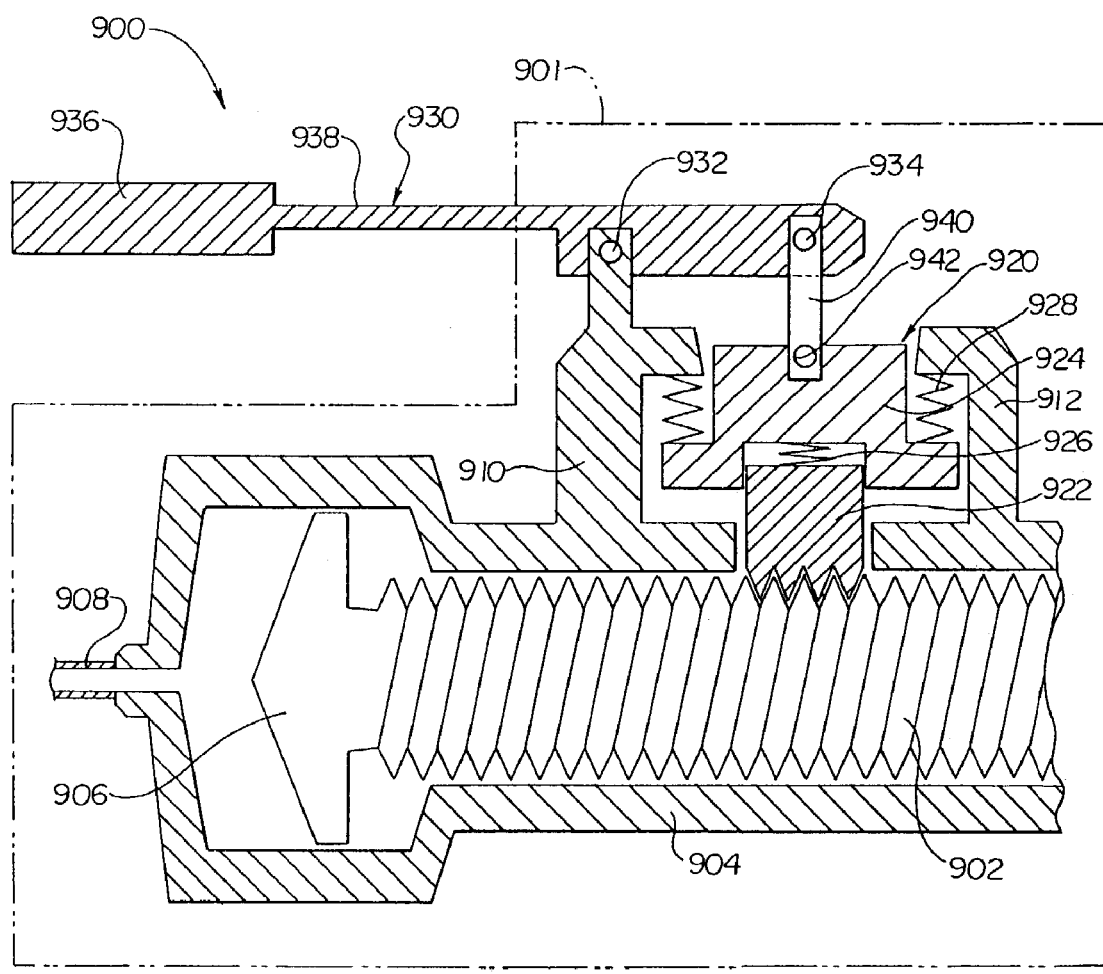
FIG. 12 is a plan view with partial cut away views of an illustrative embodiment of a pressure relief mechanism in accordance with the present invention also incorporating the improvements of FIGS. 10B–10C.

FIG. 12 is a plan view with partial cut away views of an illustrative embodiment of a pressure relief mechanism in accordance with the present invention also incorporating the improvements of FIGS. 10B–10C. Pressure relief mechanism 900 is shown with an area 901 expanded for improved detail. Threaded shaft 902 is inside cylinder 904, connected to plunger 906, and cylinder 904 ends in outlet 908. Cylinder 904 has an opening surrounded by outcroppings 910,912. Engagement mechanism 920 is disposed between outcroppings 910,912. Outcroppings 910, 912 may connect to form a circular, oval, rectangle or otherwise enclosed outcropping. The engagement mechanism includes a first part 922 which is adapted to engage the threaded shaft 902, a second part 924, and an elastic portion 926 that connects the first part 922 to the second part 924. As before, the elastic portion 926 may be of several types and forms, but is shown for simplicity and clarity as a spring. Springs 928 are biased and placed to press the engagement mechanism 920 toward the threaded shaft 902.

A lever 930 is connected to a pivot 932 secured to an outcropping of the cylinder 910. The lever 930 includes a pin 934 that connects the lever 930 to the engagement mechanism 920 via a link 940 that is connected to a pin 942 on the engagement mechanism 920 and the pin 934 on the lever 930. The lever 930 has a handle 936 and an intermediate portion 938.

In the embodiment of FIG. 12, when the lever 930 is in a first position, the link 940 enables (and in some embodiments, pushes) the engagement mechanism 920 to engage the threaded shaft 902. Springs 928 may provide additional force for pressing the engagement mechanism 920 toward threaded shaft 902 and causing engagement. When the lever 930 is moved to a second position, the link 940 transfers a force to the engagement mechanism 920, particularly the second part 924. As the force is delivered to the second part, springs 928 are compressed and second part 924 is pulled away from the threaded shaft 902. Elastic portion 926 may stretch until the force exerted by the elastic properties of the elastic portion 926 overcomes the forces holding the first part 922 to the threaded shaft 902, at which time the first part 922 will snap up to the second part 924 and away from the threaded shaft 902, protecting threads on both the threaded shaft 902 and the first part 922.

In an alternative embodiment similar to FIG. 12, the engagement mechanism 920 may not have an elastic portion 926. Instead, the lever 930, particularly the intermediate portion 938, may include elastic properties enabling the lever 930 to bend until sufficient force is transferred across the bend of the lever 930 to force the engagement mechanism 920 to snap away from the threaded shaft 902 a sufficient distance to protect the threads of the engagement mechanism 920 and the threaded shaft 902.

Figure 13:
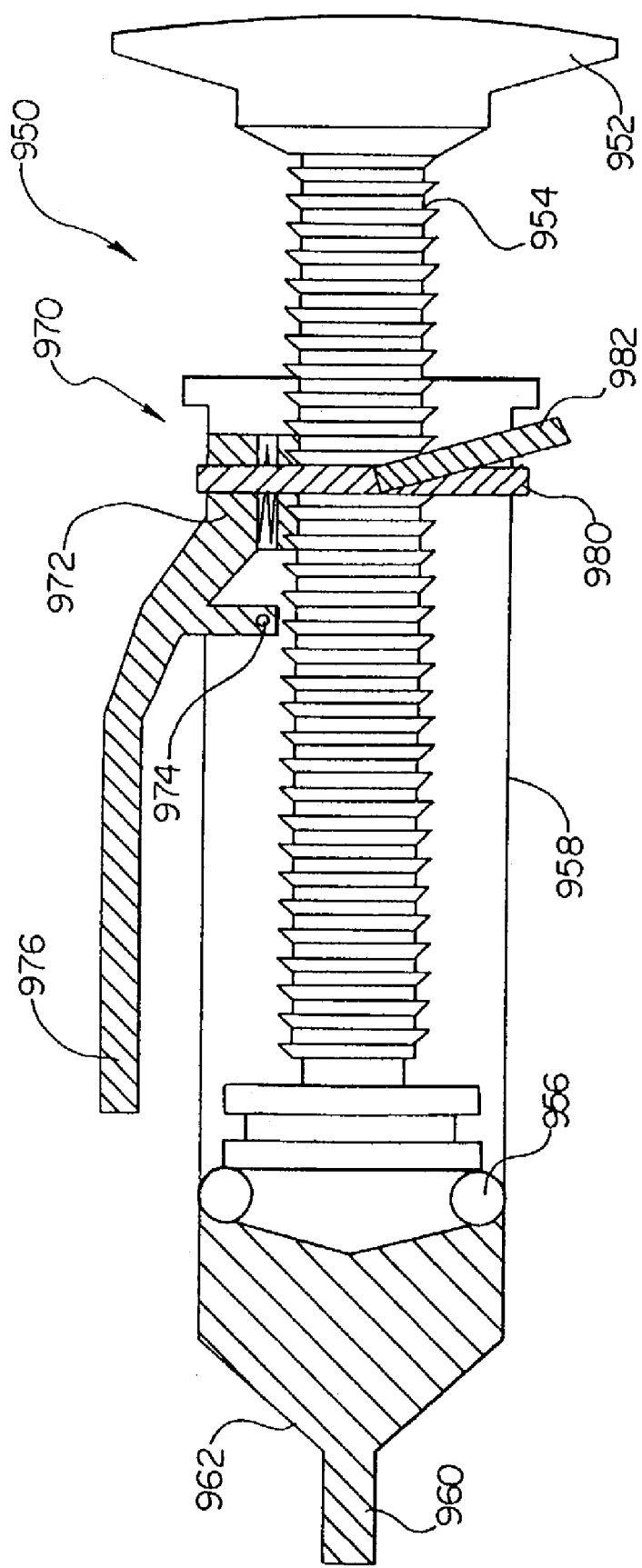
FIG. 13 is a plan view with partial cut away views of another illustrative embodiment of a pressure relief mechanism in accordance with the present invention also incorporating the improvements of FIGS. 10B–10C.

FIG. 13 is a plan view with partial cut away views of another illustrative embodiment of a pressure relief mechanism in accordance with the present invention also incorporating the improvements of FIGS. 10B–10C. In FIG. 13, syringe 950 includes a knob 952 which may turn threaded shaft 954. Threaded shaft 954 is connected to plunger 956 inside cylinder 958. Cylinder 958 includes an outlet 960, and inflation media 962 is disposed between plunger 956 and outlet 960. Pressure relief mechanism 970 is attached to syringe 950. An engagement mechanism 972 in accordance with those shown and explained in FIGS. 10–12 is disposed in an opening in cylinder 958. A lever 976 is connected to cylinder 958 by pin 974. A collar is also included, the collar including a band 980 and a buckle 982.

In the illustrative embodiment of FIG. 13, when the band 980 is in place over the engagement mechanism 972 with the buckle 982 buckled, the engagement mechanism 972 is pressed against the threaded shaft 954 so that engagement mechanism 972 and threaded shaft 954 are engaged. Unbuckling buckle 982 loosens the band 980 so that the band does not apply a force holding the engagement mechanism pressed against threaded shaft 954. However, if the engagement mechanism 972 and threaded shaft 954 are already engaged and some pressure is applied in the inflation media 962, the engagement mechanism 972 and threaded shaft 954 may remain engaged under frictional force (and other forces in some embodiments) between their respective threads. Thus, lever 976 may be depressed or otherwise moved to apply a force to the engagement mechanism 972, causing disengagement.

Figure 14:
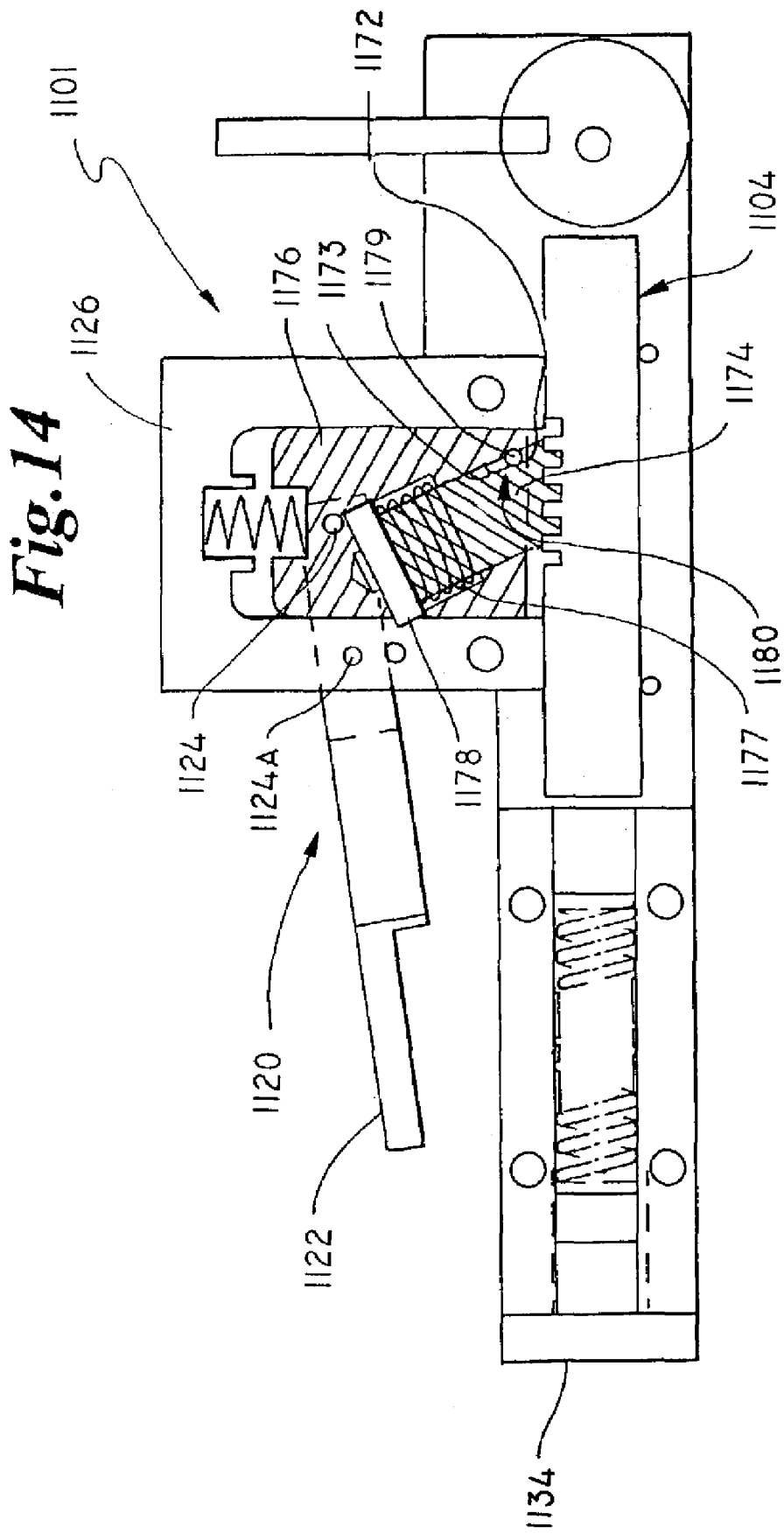
FIG. 14 is a plan view of an illustrative embodiment of a pressure relief mechanism in accordance with the present invention.

FIG. 14 is an alternative pressure relief mechanism 1101 that is similar in form and function as the other pressure relief mechanisms described herein, with a few exceptions as described below. In at least some embodiments, mechanism 1101 includes plunger 1104, engagement mechanism 1120, lever 1122, pin 1124, and collar 1126. In addition, pressure relief mechanism 1101 also includes a housing 1176 disposed at least partially within collar 1126. Housing 1176 is coupled to lever 1122 at pin 1124 (pivoting about a pin 1124A at collar 1126) such that depressing lever 1122 results in lateral movement of housing 1176 (i.e., away from the longitudinal axis of plunger 1104).

Figure 14A:
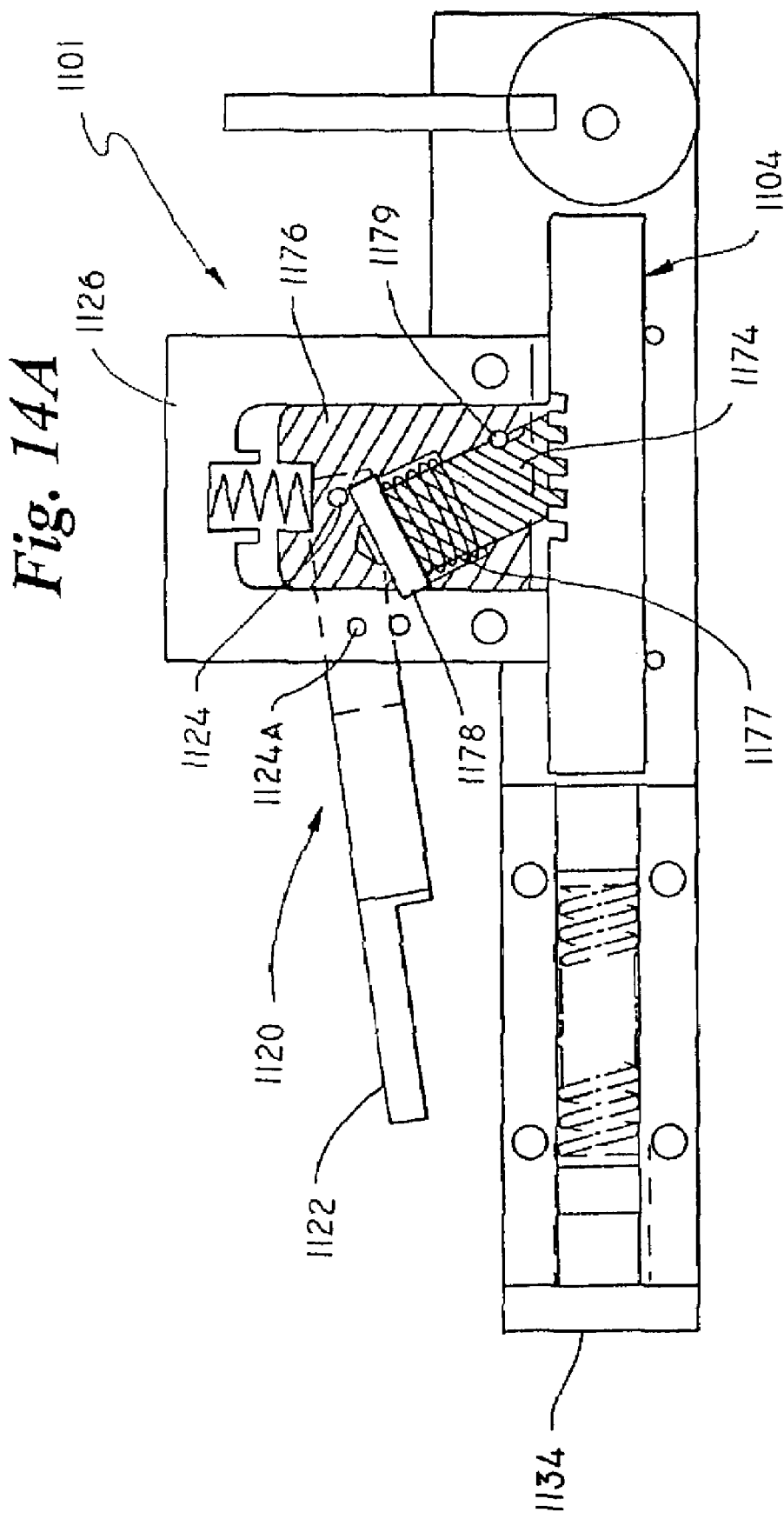
FIG. 14A is an alternative plan view of the pressure relief mechanism shown in FIG. 14.

Engagement mechanism 1120 includes a nut 1174 adapted and configured to threadably engage plunger 1104. Housing 1176 is coupled to nut 1174 by a compression spring 1177 and a pin 1179. In at least some embodiments, pin 1179 is rigidly secured to housing 1176 at one end and slidably disposed within a slot 1180 at the other end. Slot 1180 may include a first or bottom notch 1172 similar to first notch 672 described above and a second or top notch 1173 similar to second notch 673 described above. Engagement mechanism 1120 may be configured so that partially depressing lever 1122 results in lateral movement of housing 1176. Because of the secure connection between pin 1179 and housing 1176 and because of the slidable connection between pin 1179 and nut 1174, the lateral movement of housing 1176 results in pin 1179 shifting or being "pulled" within slot 1180. For example, pin 1179 may be positioned at the bottom of slot 1180 (e.g., adjacent notch 1172) prior to depressing lever 1122, and pin 1179 may shift to the top of slot 1180 (e.g., adjacent notch 1173) after partially depressing lever 1122 as shown in FIG. 14A. Because slot 1180 is oriented at an angle relative to the longitudinal axis of plunger 1104, the top and bottom of slot 1180 are separated by a longitudinal distance. Because of this longitudinal distance, shifting of pin 1179 from the bottom to the top of slot 1180 results in or otherwise allows a slight longitudinal shifting of nut 1174 and, thus, plunger 1104. As this occurs, the fluid pressure within the inflation lumen (e.g., lumen 26) and/or the barrel or outlet portion 1134 of mechanism 1101 causes plunger 1104 to move longitudinally away from outlet 1134 a distance equal to the longitudinal spacing between the lower end of slot 1180 and the upper end (e.g., from pin center to pin center). The pressure within the inflation lumen is thereby reduced (or relieved) due to the increase in volume within the fluid chamber of outlet 1134. The reduction in pressure decreases the frictional forces at the threaded connection between nut 1174 and plunger 1104, which reduces the forces required to separate nut 1174 from plunger 1104 and reduces the possibility of damage to the various components (e.g., thread on plunger 1104). With pressure reduced, lever 1122 can be further actuated to shift the position of nut 1174.

It can be appreciated that compression spring 1177 will tend to pull nut 1174 away from plunger 1104 (i.e., shift toward the second position) if allowed to expand. Without depressing lever 1122, little space exists between housing 1176 and nut 1174, which prevents spring 1177 from expanding. Lateral movement of housing 1176, however, opens up a space 1178 between housing 1176 and nut 1174 that may become large enough to permit expansion of spring 1177 and shifting of nut 1174 from the first position to the second position. With pressure at least partially relieved as described above, depressing lever 1122 results in lateral movement of housing 1176 and, eventually, the catching of pin 1179. Once pin 1179 catches, additional actuation of lever 1122 results in nut 1174 becoming at least partially disengaged with threads of the plunger 1104 as shown in FIG. 14B. The result of disengaging the threads of nut 1174 allows compression spring 1177 to pull nut 1174 laterally into space 1178, resulting in the shifting of nut 1176 from the first position to the second position.

From this design, it can be appreciated that the use of compression spring 1177 with a potential energy sufficiently great to shift nut 1176 when partially disengaged from plunger 1104 would add the benefit of a "quick release" feature to pressure relief mechanism 1101 in at least some embodiments. For example, as lever 1122 is depressed, pressure may be at least partially relieved and nut 1176 may become partially disengaged from plunger 1104. Once partially disengaged, additional pressing on lever 1122 laterally moves housing 1176, which opens space 1178. When space 1178 is sufficiently opened, compression spring 1177 can rapidly expand, pulling nut 1176 into space 1178 and disengaging nut 1176 and plunger.

Figure 15:
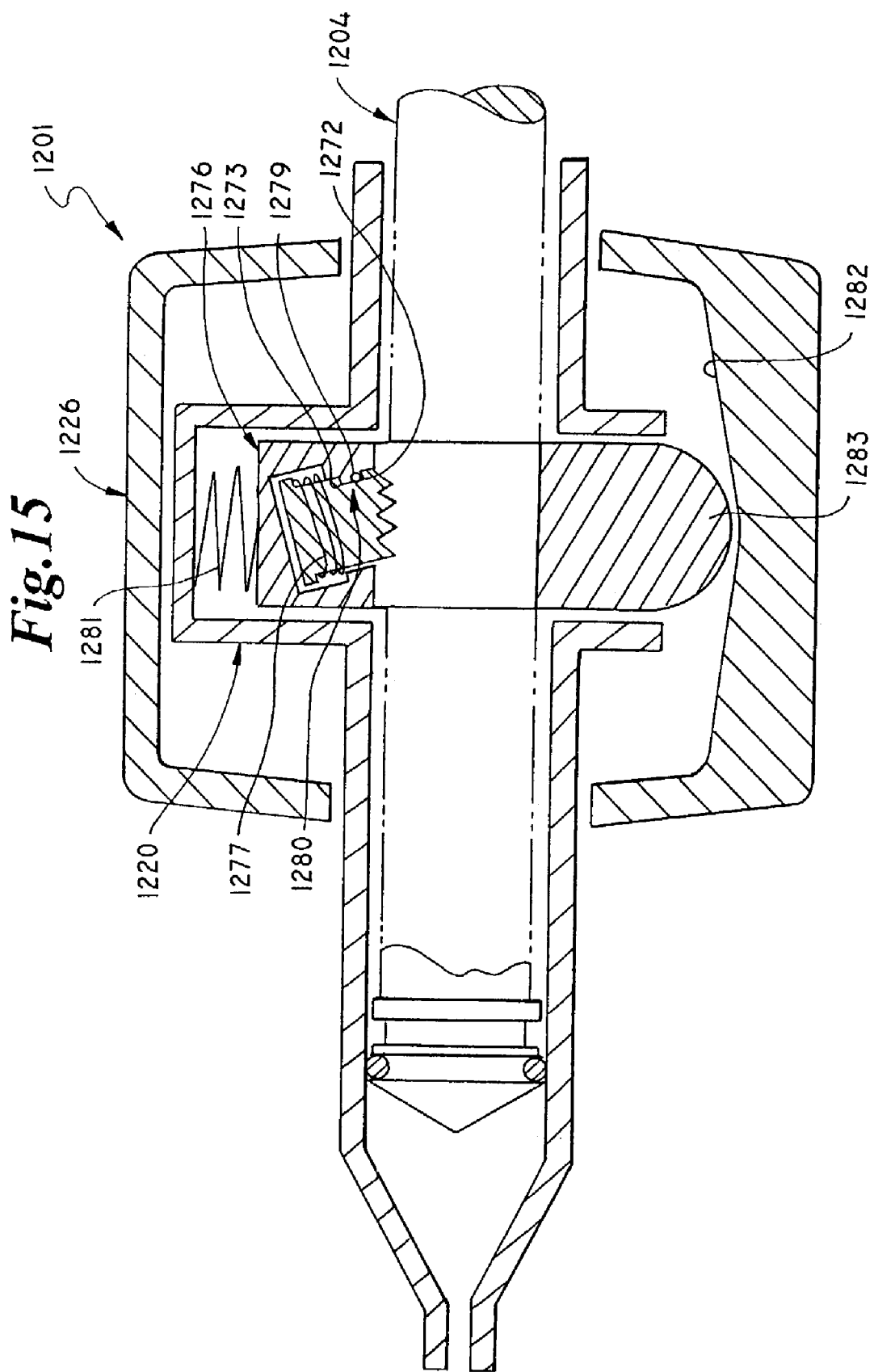
FIG. 15 is a plan view of an illustrative embodiment of a pressure relief mechanism in accordance with the present invention.

FIG. 15 is an illustration of an alternative pressure relief mechanism 1201 including plunger 1204, engagement mechanism 1220, and collar 1226. Mechanism 1201 is essentially the same in form and function as mechanism 1101, except that instead of including a lever to shift engagement mechanism 1220, collar 1226 is used.

An extension 1283 of housing 1276 is adapted for contact with an inner wall 1282 of collar 1226. Inner wall 1282 of collar 1226 is shaped so that, when collar 1226 is in a first location (as shown in FIG. 15), extension 1283 allows a spring 1281 to press housing 1276 toward engagement mechanism 1220, and when collar 1226 is in a second position (i.e., when collar is moved up or down along the longitudinal axis of plunger 1204), extension 1283 pushes against the bias of spring 1281 to move housing 1276 away from engagement mechanism 1220.

Similarly to what is described above, housing 1276 is coupled to engagement mechanism 1220 by compression spring 1277 and pin 1279, which function basically the same as compression spring 1177 and pin 1179. For example, as collar 1226 is at least partially moved, pin 1279 shifts within slot 1280. Slot 1280 is essentially the same as slot 1180 and includes notch 1272 and notch 1273 and shift can be, for example, for a position adjacent notch 1272 to a position adjacent notch 1273. This shift allows pressure within the inflation lumen to push onto and longitudinally shift plunger 1204. Additional movement of collar 1226 allows pin 1279 to catch and at least partially disengage nut 1274 from plunger 1204, and allow compression spring 1277 to expand and shift engagement mechanism 1220 into the second position.

Turning now to FIGS. 16, 17, and 18, a variety of lever configurations are shown that are appropriate for shifting an engagement mechanism between the first position and the second position and may be used in any of the embodiments illustrated above. Similar to what is shown in FIGS. 14–15, each incorporates the ability for the plunger to be longitudinally moved in order to relieve pressure. FIG. 16 depicts lever 1322 coupled to engagement mechanism 1320 including plunger 1304, pivot pin 1324, and a spring 1382. According to this embodiment, spring 1382 is biased to hold engagement mechanism 1320 in the first position (by pressing laterally on lever 1322). Depressing lever 1322 overcomes the bias of spring 1382 and shifts the position of engagement mechanism.

Also from FIG. 16, it can be appreciated that lever 1322 may include opening 1371 with first notch 1372 and second notch 1373. As described above, opening 1371 may permit shifting of engagement mechanism 1320 and plunger 1304 in order to relieve a substantial amount of pressure upon plunger 1304.

In FIG. 17, spring 1482 may be coupled to a proximal end 1483 of lever 1422. According to this embodiment, lever 1422 may be shifted in the longitudinal direction (relative to plunger 1404) so as to shift engagement mechanism 1420 between the first position and the second position. Engagement mechanism 1420 may also include one or more openings 1471 that are analogous to opening 1371.

In FIG. 18, lever 1522 includes a first pivot point 1583 and a second pivot point 1584, such that when lever 1522 is in a first configuration first pivot point 1583 is located distally and laterally of second pivot point 1584. Depressing lever 1522 to a second configuration results in a change of position of pivot point 1584 that results in proximal movement of engagement mechanism 1520 and plunger 1504. Engagement mechanism 1520 may also include one or more openings 1571 that are analogous to opening 1371.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A pressure relief mechanism for use with a balloon catheter, the pressure relief mechanism comprising:
    an inflation device including a plunger connected to a threaded shaft;
    an engagement mechanism having threads corresponding to threads on the threaded shaft, wherein the engagement mechanism is disposed with respect to the threaded shaft so that, when the engagement mechanism is in a first position, threads on the engagement mechanism threadably engage threads of the threaded shaft so that movement of the plunger requires twisting the threaded shaft, and when the engagement mechanism is in a second position, threads on the engagement mechanism are disengaged with threads of the threaded shaft so that movement of the plunger does nor require twisting the threaded shaft;
    a lever for controlling whether the engagement mechanism is in the first position or the second position;
    wherein the lever pivots about a pivot point disposed adjacent the engagement mechanism;
    wherein the lever further comprises an opening proximate the pivot point, the opening shaped to include a first notch and a second notch, the first notch being located proximally of the second notch; and
    wherein the engagement mechanism includes one or more springs biased to hold the engagement mechanism in the first position.

2. The pressure relief mechanism of claim 1, wherein the inflation device further includes an outlet port, the outlet port being in fluid communication with an inflation lumen of a balloon catheter.

3. The pressure relief mechanism of claim 1, further comprising a collar disposed proximate the engagement mechanism.

4. The pressure relief mechanism of claim 1, wherein the lever is attached to the engagement mechanism.

5. The pressure relief mechanism of claim 4, and wherein when the lever is in a first alignment, the engagement mechanism is in the first position, and when the lever is in a second aligranent, the engagement mechanism is in the second position.

6. The pressure relief mechanism of claim 1, wherein shifting the lever from the first alignment to the second alignment overcomes the bias of the spring and results in the engagement mechanism shifting from the first position to the second position.

7. The pressure relief mechanism of claim 1, wherein partial or complete shifting of the lever from the first alignment to the second alignment results in the lever pivot point shifting from the first notch to the second notch, resulting in the proximal movement of both the engagement mechanism and the plunger.

8. The pressure relief mechanism of claim 1, further comprising a housing disposed at least partially within the collar, the housing coupled to the lever such that shifting the lever from the first alignment to the second alignment results in lateral movement of the housing.

9. The pressure relief mechanism of claim 8, wherein the housing is coupled to the engagement mechanism by a compression spring, and wherein shifting the lever from the first alignment to the second alignment results in lateral motion of the housing that opens up a space between the housing and the engagement mechanism.

10. The pressure relief mechanism of claim 9, further comprising a pin coupling the housing to the engagement mechanism such that partial shifting of the lever toward the second alignment results in an amount of lateral movement of the housing sufficient to result in the pin catching, and such that additional shifting of the lever toward the second alignment results in the engagement mechanism becoming at least partially disengaged from threads of the plunger.

11. The pressure relief mechanism of claim 10, wherein the engagement mechanism and threads of the plunger remain engaged after lateral motion of the housing sufficient to partially disengage the engagement mechanism from threads of the plunger because of frictional forces between the threads of the engagement mechanism and threads of the plunger.

12. The pressure relief mechanism of claim 11, wherein the result of partially disengaging the threads of the engagement object from threads of the plunger by the pin overcomes the frictional forces and allows the compression spring to pull the engagement object laterally within the space, resulting in the shifting of the engagement mechanism from the first position to the second position.

13. The pressure relief mechanism of claim 12, wherein the compression spring has a potential energy, and wherein the potential energy is sufficiently great such that shifting of the engagement object from the first position to the second position occurs relatively quickly.

14. The pressure relief mechanism of claim 1, wherein the lever is coupled to a longitudinal spring such that moving the lever in a direction parallel to a longitudinal axis of the plunger shifts the engagement mechanism between the first position and the second position.

15. The pressure relief mechanism of claim 1, wherein the lever comprises a first pivot point and a second pivot point, such that when the lever is in a first configuration the first pivot point is located distally and laterally of the second pivot point, and wherein shifting the lever to a second configuration results in a change of position of both pivot points that results in proximal movement of engagement mechanism and the plunger.

* * * * *

UNITED STATES PATENT AND TRADEMARK OFFICE
CERTIFICATE OF CORRECTION

| | | |
|---|---|---|
| PATENT NO. | : 7,207,971 B2 | Page 1 of 1 |
| APPLICATION NO. | : 10/328372 | |
| DATED | : April 24, 2007 | |
| INVENTOR(S) | : Colin P. Hart et al. | |

It is certified that error appears in the above-identified patent and that said Letters Patent is hereby corrected as shown below:

Column 15
Line 22, delete "nor" and insert therefor -- not --.
Line 47, delete "aligranent" and insert therefor -- alignment --.

Signed and Sealed this

Nineteenth Day of June, 2007

JON W. DUDAS
*Director of the United States Patent and Trademark Office*